US011833185B2

(12) United States Patent
Bradley et al.

(10) Patent No.: US 11,833,185 B2
(45) Date of Patent: Dec. 5, 2023

(54) ANTI-NEURODEGENERATIVE THERAPEUTIC, METHOD OF MANUFACTURE, AND USE

(71) Applicant: UNIVERSITY OF KENTUCKY RESEARCH FOUNDATION, Lexington, KY (US)

(72) Inventors: Luke H. Bradley, Lexington, KY (US); Don M. Gash, Lexington, KY (US); Greg A. Gerhardt, Lexington, KY (US); Raymond T. Bartus, Sr., San Diego, CA (US)

(73) Assignee: UNIVERSITY OF KENTUCKY RESEARCH FOUNDATION, Lexington, KY (US)

( * ) Notice: Subject to any disclaimer, the term of this patent is extended or adjusted under 35 U.S.C. 154(b) by 0 days.

(21) Appl. No.: 16/788,123

(22) Filed: Feb. 11, 2020

(65) Prior Publication Data

US 2020/0282007 A1 Sep. 10, 2020
US 2021/0260149 A9 Aug. 26, 2021

Related U.S. Application Data

(63) Continuation-in-part of application No. PCT/US2018/046491, filed on Aug. 13, 2018.

(60) Provisional application No. 62/544,046, filed on Aug. 11, 2017.

(51) Int. Cl.
| A61K 38/08 | (2019.01) |
| A61P 25/28 | (2006.01) |
| A61P 25/06 | (2006.01) |
| A61P 25/24 | (2006.01) |
| A61P 25/16 | (2006.01) |

(52) U.S. Cl.
CPC .............. *A61K 38/08* (2013.01); *A61P 25/16* (2018.01); *A61P 25/24* (2018.01); *A61P 25/28* (2018.01)

(58) Field of Classification Search
CPC .......... A61K 38/08; A61P 25/16; A61P 25/24; A61P 25/28
See application file for complete search history.

(56) References Cited

U.S. PATENT DOCUMENTS

| 7,214,786 | B2 * | 5/2007 | Kovalic | C12N 15/8261 |
| | | | | 536/23.6 |
| 9,402,875 | B2 | 8/2016 | Bradley et al. | |
| 9,586,992 | B2 | 3/2017 | Bradley et al. | |
| 10,501,731 | B2 * | 12/2019 | Steward | A61P 5/00 |
| 2003/0186214 | A1 | 10/2003 | Yan et al. | |
| 2010/0035820 | A1 | 2/2010 | Bradley et al. | |
| 2011/0178025 | A1 | 7/2011 | Bradley et al. | |
| 2011/0309831 | A1 | 12/2011 | Brown et al. | |
| 2013/0330335 | A1 * | 12/2013 | Bremel | A61P 37/04 |
| | | | | 435/69.6 |
| 2014/0148393 | A1 | 5/2014 | Bradley et al. | |
| 2015/0322165 | A1 * | 11/2015 | Cheong | C07K 16/40 |
| | | | | 435/69.6 |
| 2016/0074463 | A1 | 3/2016 | Laruelle et al. | |
| 2016/0228470 | A1 | 8/2016 | Jeon et al. | |
| 2016/0367462 | A1 | 12/2016 | Samain | |
| 2016/0367463 | A1 | 12/2016 | Idkowiak-Baldys et al. | |
| 2017/0173108 | A1 | 6/2017 | Bradley et al. | |

FOREIGN PATENT DOCUMENTS

| WO | 96/39179 A1 | 12/1996 |
| WO | 03/062262 A2 | 7/2003 |
| WO | 03/063760 A2 | 8/2003 |

OTHER PUBLICATIONS

Baert et al., "Influence of Immunogenicity on the Long-Term Efficacy of Infliximab in Crohn's Disease," The New England Journal of Medicine, 2003, pp. 601-608, vol. 348.
Baker et al., "Immunogenicity of protein therapeutics: The key causes, consequences and challenges," Self/Nonself, 2010, pp. 314-322, vol. 1, No. 4.
Bendtzen et al., "Individualized Monitoring of Drug Bioavailability and Immunogenicity in Rheumatoid Arthritis Patients Treated With the Tumor Necrosis Factor α Inhibitor Infliximab," Arthritis & Rheumatism, 2006, pp. 3782-3789, vol. 54, No. 12.
Brooks et al., "Significance of immune response to enzyme-replacement therapy for patients with a lysosomal storage disorder," Trends in Molecular Medicine, 2003, pp. 450-453, vol. 9, No. 10.
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," The Journal of Cell Biology, 1990, pp. 2129-2138, vol. 111.
Büttel et al., "Taking immunogenicity assessment of therapeutic proteins to the next level," Biologicals, 2011, pp. 100-109, vol. 39.
Casadevall et al., "Pure Red-Cell Aplasia and Antierythropoietin Antibodies in Patients Treated With Recombinant Erythropoietin," The New England Journal of Medicine, 2002, pp. 469-475, vol. 346, No. 7.

(Continued)

*Primary Examiner* — Olga N Chernyshev
(74) *Attorney, Agent, or Firm* — POLSINELLI PC; Tara A. Nealey

(57) ABSTRACT

Therapeutic peptides of the following sequence are disclosed: $Xaa_1$-$Xaa_2$-$Xaa_3$-$Xaa_4$-$Xaa_5$, and optionally further comprising $Xaa_6$, wherein Xaa represents an amino acid; $Xaa_3$ is proline; and subscripts represent the positions of each amino acid in the peptide sequence starting from the amino terminus of said peptide extending to the C-terminus. A therapeutic peptide optionally includes a linker that cyclizes the peptide. Also described are methods of treating a neurodegenerative disorder and/or injury in a human subject in need of such treatment by administering to the subject a therapeutically effective amount of a therapeutic peptide as disclosed herein.

6 Claims, 22 Drawing Sheets
Specification includes a Sequence Listing.

(56) References Cited

OTHER PUBLICATIONS

Chapman et al., "Intranasal Treatment of Central Nervous System Dysfunction in Humans," Pharm Res, 2013, pp. 2475-2484, vol. 30.
Cheng et al., "An intranasally delivered peptide drug ameliorates cognitive decline in Alzheimer transgenic mice," EMBO Molecular Medicine, 2017, pp. 703-715, vol. 9.
Choi et al., "Specific modulation of dopamine expression in neuronal hybrid cells by primary cells from different brain regions," Proc. Natl. Acad. Sci. USA, 1992, pp. 8943-8947, vol. 89.
Davies, "The Cyclization of Peptides and Depsipeptides," Journal of Peptide Science, 2003, pp. 471-501, vol. 9, No. 8.
Djupesland, "Nasal drug delivery devices: characteristics and performance in a clinical perspective—a review," Drug Deliv. and Transl. Res., 2013, pp. 42-62, vol. 3, No. 1.
Durelli et al., "Anti-Interferon Antibodies in Multiple Sclerosis. Molecular Basis and Their Impact on Clinical Efficacy," Frontiers in Bioscience, 2004, pp. 2192-2204, vol. 9.
Fineman et al., "Chapter 6—Clinical Relevance of Anti-exenatide Antibodies: Safety, Efficacy, and Cross-reactivity with Long-term Treatment," Diabetes, Obesity, and Metabolism, 2012, pp. 85-99.
Fortuna et al., "Intranasal delivery of systemic-acting drugs: small-molecules and biomacromolecules," Accepted Manuscript, European Journal of Pharmaceutics and Biopharmaceutics, (2014), doi:http://dx.doi.org/10.1016/j.ejpb.2014.03.004, 56 pgs.
Hansel et al., "The safety and side effects of monoclonal antibodies," Nature Reviews Drug Discovery, 2010, pp. 325-338, vol. 9.
Hanson et al., "Intranasal Administration of CNS Therapeutics to Awake Mice," Journal of Visualized Experiments, 2013, e4440, pp. 1-7, vol. 74.
Joo, "Cyclic Peptides as Therapeutic Agents and Biochemical Tools," Biomolecules & Therapeutics, 2012, pp. 19-26, vol. 20, No. 1.
Kim et al., "Immune epitope database analysis resource," Nucleic Acids Research, 2012, pp. W525-W530, vol. 40.
Krishna et al., "Immunogenicity to Biotherapeutics—The Role of Anti-drug Immune Complexes," Frontiers in Immunology, 2016, pp. 1-13, vol. 7, No. 21.
Lazar et al., "Transforming Growth Factor α: Mutation of Aspartic Acid 47 and Leucine 48 Results in Different Biological Activities," Molecular and Cellular Biology, 1988, pp. 1247-1252, vol. 8, No. 3.
Leach et al., "Immunogenicity/Hypersensitivity of Biologics," Toxicologic Pathology, 2014, pp. 293-300, vol. 42, No. 1.
Lin et al., "Structure-Function Relationships in Glucagon: Properties of Highly Purified Des-His1-, Monoiodo-, and [Des-Asn28, Thr29](homoserine lactone27)-glucagon," Biochemistry, 1975, pp. 1559-1563, vol. 14, No. 8.
Lukhanina et al., "Effect of cerebrolysin on the electroencephalographic indices of brain activity in Parkinson's disease," Zh Nevrol Psikhatr Im S S Korsakova 104: 54-60 (2004). Abstract Only.
Ma et al., "A new mutation in BFSP2 (G1091A) causes autosomal dominant congenital lamellar cataracts," Molecular Vision, 2008, pp. 1906-1911, vol. 14.
Meredith et al., "Intranasal Delivery of Proteins and Peptides in the Treatment of Neurodegenerative Diseases," The AAPS Journal, 2015, pp. 780-787, vol. 17, No. 4.
Newman et al., "Drug Delivery to the Nasal Cavity: In Vitro and In Vivo Assessment," Critical Reviews in Therapeutic Drug Carrier Systems, 2004, pp. 21-66, vol. 21, No. 1.
Ohshima-Hosoyama et al., "A Monoclonal Antibody-GDNF Fusion Protein Is Not Neuroprotective and Is Associated with Proliferative Pancreatic Lesions in Parkinsonian Monkeys," PLoS One, 2012, e39036, pp. 1-14, vol. 7, No. 6.
Prescott et al., "The Inhibitor Antibody Response Is More Complex in Hemophilia A Patients Than in Most Nonhemophiliacs With Factor VIII Autoantibodies," Blood, 1997, pp. 3663-3671, vol. 89, No. 10.
Richards et al., "Phase I Evaluation of Humanized OKT3: Toxicity and Immunomodulatory Effects of hOKT3γ4," Cancer Research, 1999, pp. 2096-2101, vol. 59.
Rojko et al., "Formation, Clearance, Deposition, Pathogenicity, and Identification of Biopharmaceutical-related Immune Complexes: Review and Case Studies," Toxicologic Pathology, 2014, pp. 725-764, vol. 42, No. 4.
Scharrer, "Recombinant factor VIIa for patients with inhibitors to factor VIII or IX or factor VII deficiency," Haemophilia, 1999, pp. 253-259, vol. 5.
Schellekens, "The Immunogenicity of Therapeutic Proteins," Discov Med., 2010, pp. 560-564, vol. 9.
Schmidt et al., "Immunogenicity of rituximab in patients with severe pemphigus," Clinical Immunology, 2009, pp. 334-341, vol. 132.
Schwartz et al., "A superactive insulin: [B10-Aspartic acid]insulin(human)," Proc. Natl. Acad. Sci. USA, 1987, pp. 6408-6411, vol. 84.
Sies, "Hydrogen peroxide as a central redox signaling molecule in physiological oxidative stress: Oxidative eustress," Redox Biology, 2017, pp. 613-619, vol. 11.
Spetter et al., "Intranasal Neuropeptide Administration To Target the Human Brain in Health and Disease," Molecular Pharmaceutics, 2015, pp. 2767-2780, vol. 12, No. 8.
Stoever et al., "Inhaled Insulin and Insulin Antibodies: A New Twist to an Old Debate," Diabetes Technology & Therapeutics, 2002, pp. 157-161, vol. 4, No. 2.
Tatarewicz et al., "Development of a Maturing T-Cell-Mediated Immune Response in Patients with Idiopathic Parkinson's Disease Receiving r-metHuGDNF Via Continuous Intraputaminal Infusion," Journal of Clinical Immunology, 2007, pp. 620-627, vol. 27.
Thorne et al., "Delivery of Interferon-β to the Monkey Nervous System Following Intranasal Administration," Neuroscience, 2008, pp. 785-797, vol. 152.
Wagner et al., "Consequences of Immunogenicity to the Therapeutic Monoclonal Antibodies ReoPro and Remicade," Dev Biol. (Basel, Karger), 2003, pp. 37-53, vol. 112.
Weber et al., "Antioxidants, Supplements, and Parkinson's Disease," The Annals of Pharmacotherapy, 2006, pp. 935-938, vol. 40.
Wermeling et al., "Pharmacokinetics, Bioequivalence, and Spray Weight Reproducibility of Intranasal Butorphanol After Administration With 2 Different Nasal Spray Pumps," Journal of Clinical Pharmacology, 2005, pp. 969-973, vol. 45.
Wriggers et al., "Control of Protein Functional Dynamics by Peptide Linkers," Biopolymers (Peptide Science), 2005, pp. 736-746, vol. 80.
European Search Report issued in related European Application No. 18843353.6, dated Aug. 12, 2021; 16 pgs.
Chalifour et al., "Stereoselective Interactions of Peptide Inhibitors with the β-Amyloid Peptide", The Journal of Biological Chemistry, 2003, pp. 34874-34881, vol. 278, No. 37.
Heimer et al., "Synthesis, purification and characterization of thymosin α11, a new thymic peptide", International Journal of Peptide and Protein Research, 1985, pp. 330-335, vol. 25, No. 3.
Prusakov et al., "Synthesis of Gastrin Terminal Fragments and Their Coupling to Proteins", Bioorganicheskaya Khimiya, Izdatel 'Stvo Nauka, RU, Jan. 1979, pp. 497-507, vol. 5, No. 4.
International Search Report and Written Opinion relating to International Application No. PCT/US2018/046491, dated Dec. 14, 2018; 12 pgs.

* cited by examiner

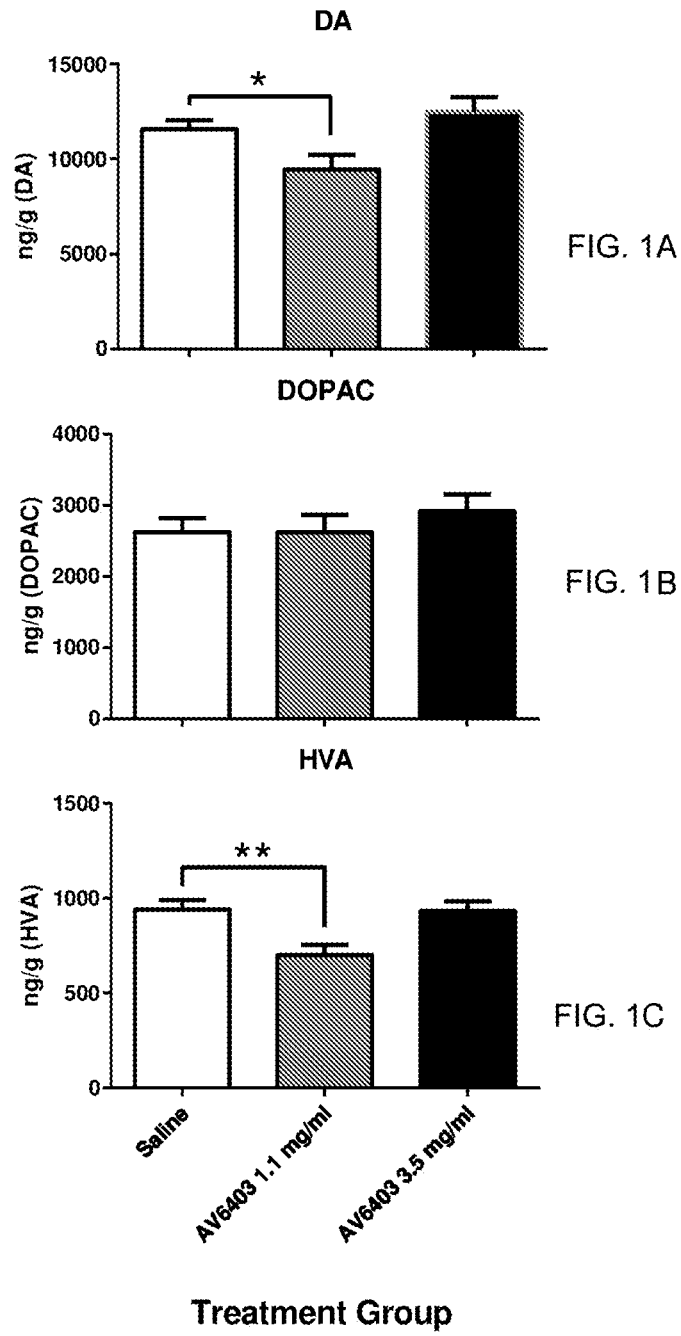

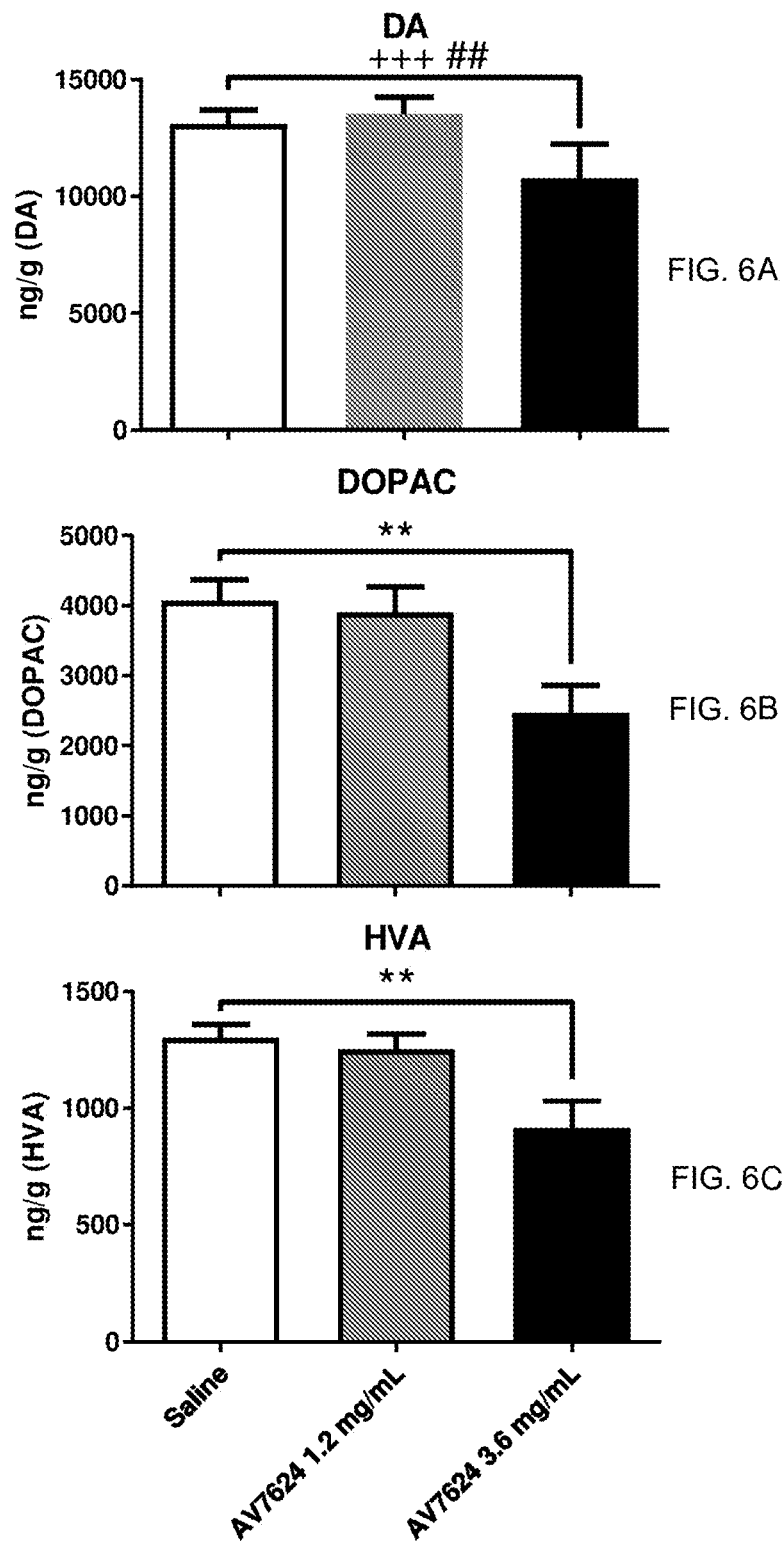

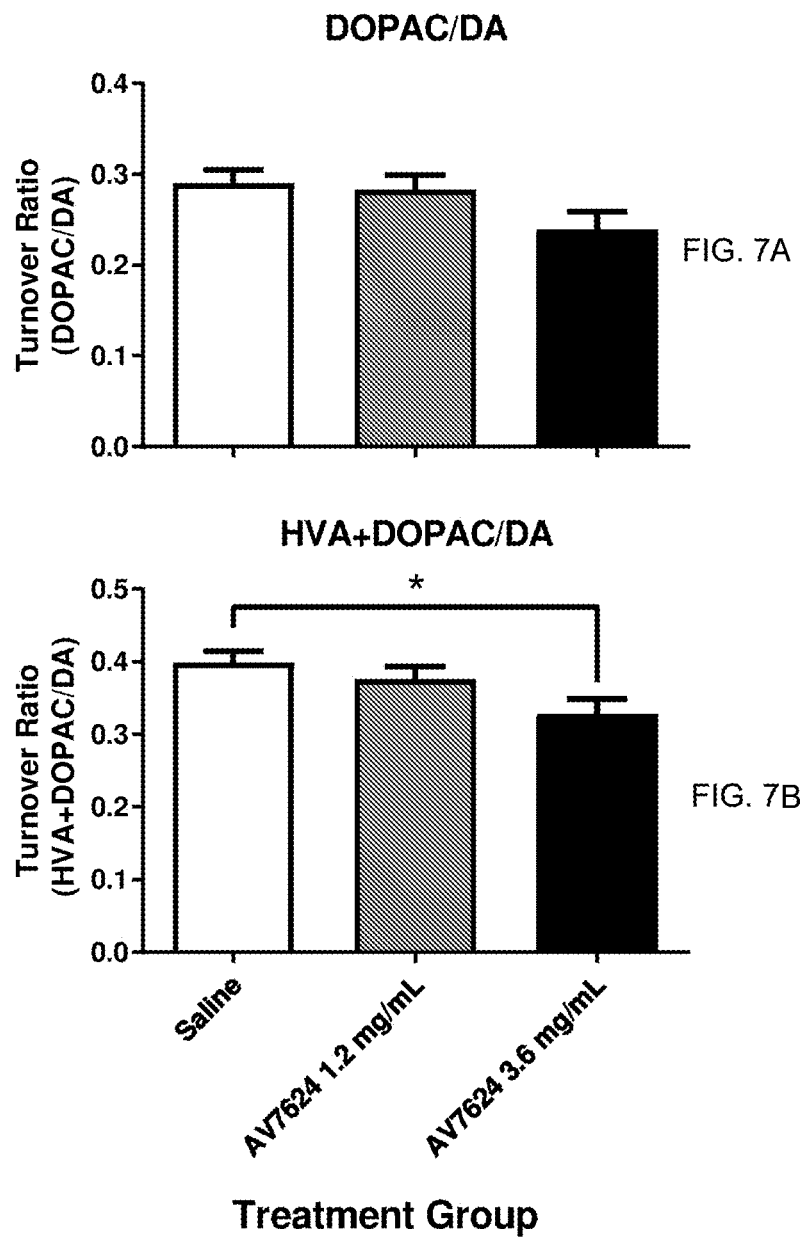

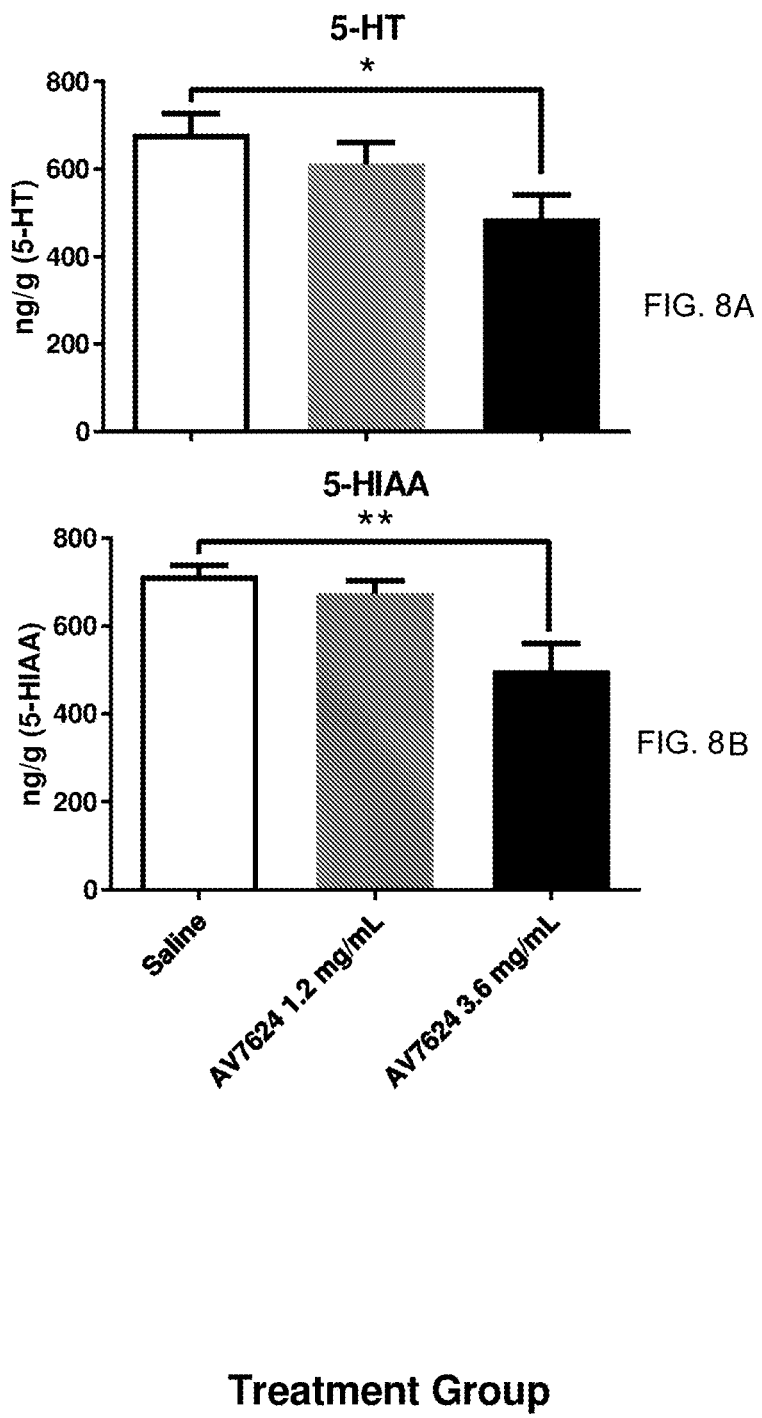

SEQUENCE LISTING

<160> NUMBER OF SEQ ID NOS: 40

<210> SEQ ID NO 1
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: AMIDATION

<400> SEQUENCE: 1

Leu Ala Pro Ala Glu Asp
1               5

<210> SEQ ID NO 2

```
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: AMIDATION

<400> SEQUENCE: 2

Glu Ala Pro Phe Glu Asp
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: AMIDATION

<400> SEQUENCE: 3

Leu Ala Pro Tyr Glu Asp
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: AMIDATION can be either present or absent at
      position 6

<400> SEQUENCE: 4

Leu Gly Pro Phe Ser Glu
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic

<400> SEQUENCE: 5

Cys Leu Gly Pro Phe Ser Glu Cys
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa is D-Ala
<220> FEATURE:
<221> NAME/KEY: MISC_FEATURE
<222> LOCATION: (4)..(4)
<223> OTHER INFORMATION: Xaa is D-Lys
<220> FEATURE:
```

```
<221> NAME/KEY: MISC_FEATURE
<222> LOCATION: (5)..(5)
<223> OTHER INFORMATION: AMIDATION

<400> SEQUENCE: 6

Trp Xaa Pro Xaa Asp
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is D-Glu
<220> FEATURE:
<221> NAME/KEY: MISC_FEATURE
<222> LOCATION: (5)..(5)
<223> OTHER INFORMATION: Xaa is D-Ala
<220> FEATURE:
<221> NAME/KEY: MISC_FEATURE
<222> LOCATION: (6)..(6)
<223> OTHER INFORMATION: AMIDATION

<400> SEQUENCE: 7

Xaa Ala Pro Phe Xaa Gly
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa is deuterated Lys
<220> FEATURE:
<221> NAME/KEY: MISC_FEATURE
<222> LOCATION: (4)..(4)
<223> OTHER INFORMATION: Xaa is D-Phe
<220> FEATURE:
<221> NAME/KEY: MISC_FEATURE
<222> LOCATION: (5)..(5)
<223> OTHER INFORMATION: Xaa is deuterated leu
<220> FEATURE:
<221> NAME/KEY: MISC_FEATURE
<222> LOCATION: (5)..(5)
<223> OTHER INFORMATION: AMIDATION

<400> SEQUENCE: 8

Glu Xaa Pro Xaa Xaa
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is acylated-Leu
<220> FEATURE:
<221> NAME/KEY: MISC_FEATURE
<222> LOCATION: (2)..(2)
<223> OTHER INFORMATION: Xaa is D-Met
<220> FEATURE:
```

```
<221> NAME/KEY: MISC_FEATURE
<222> LOCATION: (5)..(5)
<223> OTHER INFORMATION: Xaa is deuterated Ser

<400> SEQUENCE: 9

Xaa Xaa Pro Ala Xaa Phe
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: AMIDATION

<400> SEQUENCE: 10

Glu Ala Pro Ala Glu
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: AMIDATION

<400> SEQUENCE: 11

Glu Ala Pro Ala Glu Asp
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is leucine, tryptophan, or glutamate.
<220> FEATURE:
<221> NAME/KEY: MISC_FEATURE
<222> LOCATION: (2)..(2)
<223> OTHER INFORMATION: Xaa is glycine, lysine, leucine, methionine,
      tryptophan, or alanine.
<220> FEATURE:
<221> NAME/KEY: MISC_FEATURE
<222> LOCATION: (3)..(3)
<223> OTHER INFORMATION: Xaa is proline.
<220> FEATURE:
<221> NAME/KEY: MISC_FEATURE
<222> LOCATION: (4)..(4)
<223> OTHER INFORMATION: Xaa is phenylalanine, lysine, leucine,
      tryptophan, tyrosine, or alanine.
<220> FEATURE:
<221> NAME/KEY: MISC_FEATURE
<222> LOCATION: (5)..(5)
<223> OTHER INFORMATION: Xaa is alanine, cysteine, aspartate, leucine,
      methionine, asparagine, serine, or glutamate.

<400> SEQUENCE: 12

Xaa Xaa Xaa Xaa Xaa
1               5
```

```
<210> SEQ ID NO 13
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is leucine, tryptophan, or glutamate.
<220> FEATURE:
<221> NAME/KEY: MISC_FEATURE
<222> LOCATION: (2)..(2)
<223> OTHER INFORMATION: Xaa is glycine, lysine, leucine, methionine,
      tryptophan, or alanine.
<220> FEATURE:
<221> NAME/KEY: MISC_FEATURE
<222> LOCATION: (3)..(3)
<223> OTHER INFORMATION: Xaa is proline.
<220> FEATURE:
<221> NAME/KEY: MISC_FEATURE
<222> LOCATION: (4)..(4)
<223> OTHER INFORMATION: Xaa is phenylalanine, lysine, leucine,
      tryptophan, tyrosine, or alanine.
<220> FEATURE:
<221> NAME/KEY: MISC_FEATURE
<222> LOCATION: (5)..(5)
<223> OTHER INFORMATION: Xaa is alanine, cysteine, aspartate, leucine,
      methionine, asparagine, serine, or glutamate.
<220> FEATURE:
<221> NAME/KEY: MISC_FEATURE
<222> LOCATION: (6)..(6)
<223> OTHER INFORMATION: Xaa is alanine, cysteine, glutamate,
      phenylalanine, glycine, leucine, proline, serine, or aspartate.

<400> SEQUENCE: 13

Xaa Xaa Xaa Xaa Xaa Xaa
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic

<400> SEQUENCE: 14

Trp Ala Pro Ala Glu Asp
1               5

<210> SEQ ID NO 15
<211> LENGTH: 6
<212> TYPE: PRT
<213> ORGANISM: Artificial Sequence
<220> FEATURE:
<223> OTHER INFORMATION: Synthetic

<400> SEQUENCE: 15

Glu Gly Pro Ala Glu Asp
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic

<400> SEQUENCE: 16

Glu Lys Pro Ala Glu Asp
1               5
```

<210> SEQ ID NO 17
<211> LENGTH: 6
<212> TYPE: PRT
<213> ORGANISM: Artificial Sequence
<220> FEATURE:
<223> OTHER INFORMATION: Synthetic

<400> SEQUENCE: 17

Glu Leu Pro Ala Glu Asp
1               5

<210> SEQ ID NO 18
<211> LENGTH: 6
<212> TYPE: PRT
<213> ORGANISM: Artificial Sequence
<220> FEATURE:
<223> OTHER INFORMATION: Synthetic

<400> SEQUENCE: 18

Glu Met Pro Ala Glu Asp
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic

<400> SEQUENCE: 19

Glu Trp Pro Ala Glu Asp
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic

<400> SEQUENCE: 20

Glu Ala Pro Lys Glu Asp
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic

<400> SEQUENCE: 21

Glu Ala Pro Leu Glu Asp
1               5

<210> SEQ ID NO 22
<211> LENGTH: 6
<212> TYPE: PRT
<213> ORGANISM: Artificial Sequence
<220> FEATURE:
<223> OTHER INFORMATION: Synthetic

<400> SEQUENCE: 22

Glu Ala Pro Trp Glu Asp
1               5

```
<210> SEQ ID NO 23
<211> LENGTH: 6
<212> TYPE: PRT
<213> ORGANISM: Artificial Sequence
<220> FEATURE:
<223> OTHER INFORMATION: Synthetic

<400> SEQUENCE: 23

Glu Ala Pro Ala Ala Asp
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic

<400> SEQUENCE: 24

Glu Ala Pro Ala Cys Asp
1               5

<210> SEQ ID NO 25
<211> LENGTH: 6
<212> TYPE: PRT
<213> ORGANISM: Artificial Sequence
<220> FEATURE:
<223> OTHER INFORMATION: Synthetic

<400> SEQUENCE: 25

Glu Ala Pro Ala Asp Asp
1               5

<210> SEQ ID NO 26
<211> LENGTH: 6
<212> TYPE: PRT
<213> ORGANISM: Artificial Sequence
<220> FEATURE:
<223> OTHER INFORMATION: Synthetic

<400> SEQUENCE: 26

Glu Ala Pro Ala Leu Asp
1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic

<400> SEQUENCE: 27

Glu Ala Pro Ala Met Asp
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic

<400> SEQUENCE: 28

Glu Ala Pro Ala Asn Asp
1               5
```

```
<210> SEQ ID NO 29
<211> LENGTH: 6
<212> TYPE: PRT
<213> ORGANISM: Artificial Sequence
<220> FEATURE:
<223> OTHER INFORMATION: Synthetic

<400> SEQUENCE: 29

Glu Ala Pro Ala Ser Asp
1               5

<210> SEQ ID NO 30
<211> LENGTH: 6
<212> TYPE: PRT
<213> ORGANISM: Artificial Sequence
<220> FEATURE:
<223> OTHER INFORMATION: Synthetic

<400> SEQUENCE: 30

Glu Ala Pro Ala Glu Ala
1               5

<210> SEQ ID NO 31
<211> LENGTH: 6
<212> TYPE: PRT
<213> ORGANISM: Artificial Sequence
<220> FEATURE:
<223> OTHER INFORMATION: Synthetic

<400> SEQUENCE: 31

Glu Ala Pro Ala Glu Cys
1               5

<210> SEQ ID NO 32
<211> LENGTH: 6
<212> TYPE: PRT
<213> ORGANISM: Artificial Sequence
<220> FEATURE:
<223> OTHER INFORMATION: Synthetic

<400> SEQUENCE: 32

Glu Ala Pro Ala Glu Glu
1               5

<210> SEQ ID NO 33
<211> LENGTH: 6
<212> TYPE: PRT
<213> ORGANISM: Artificial Sequence
<220> FEATURE:
<223> OTHER INFORMATION: Synthetic

<400> SEQUENCE: 33

Glu Ala Pro Ala Glu Phe
1               5

<210> SEQ ID NO 34
<211> LENGTH: 6
<212> TYPE: PRT
<213> ORGANISM: Artificial Sequence
<220> FEATURE:
<223> OTHER INFORMATION: Synthetic

<400> SEQUENCE: 34

Glu Ala Pro Ala Glu Gly
1               5

<210> SEQ ID NO 35
```

```
<211> LENGTH: 6
<212> TYPE: PRT
<213> ORGANISM: Artificial Sequence
<220> FEATURE:
<223> OTHER INFORMATION: Synthetic

<400> SEQUENCE: 35

Glu Ala Pro Ala Glu Leu
1               5

<210> SEQ ID NO 36
<211> LENGTH: 6
<212> TYPE: PRT
<213> ORGANISM: Artificial Sequence
<220> FEATURE:
<223> OTHER INFORMATION: Synthetic

<400> SEQUENCE: 36

Glu Ala Pro Ala Glu Pro
1               5

<210> SEQ ID NO 37
<211> LENGTH: 6
<212> TYPE: PRT
<213> ORGANISM: Artificial Sequence
<220> FEATURE:
<223> OTHER INFORMATION: Synthetic

<400> SEQUENCE: 37

Glu Ala Pro Ala Glu Ser
1               5

<210> SEQ ID NO 38
<211> LENGTH: 5
<212> TYPE: PRT
<213> ORGANISM: Artificial Sequence
<220> FEATURE:
<223> OTHER INFORMATION: Synthetic

<400> SEQUENCE: 38

Glu Gly Pro Ala Ala
1               5

<210> SEQ ID NO 39
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: Xaa is any amino acid.
<220> FEATURE:
<221> NAME/KEY: MISC_FEATURE
<222> LOCATION: (3)..(3)
<223> OTHER INFORMATION: Xaa is proline.
<220> FEATURE:
<221> NAME/KEY: MISC_FEATURE
<222> LOCATION: (4)..(5)
<223> OTHER INFORMATION: Xaa is any amino acid.

<400> SEQUENCE: 39

Xaa Xaa Xaa Xaa Xaa
1               5

<210> SEQ ID NO 40
<211> LENGTH: 6
<212> TYPE: PRT
```

```
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: Xaa is any amino acid.
<220> FEATURE:
<221> NAME/KEY: MISC_FEATURE
<222> LOCATION: (3)..(3)
<223> OTHER INFORMATION: Xaa is proline.
<220> FEATURE:
<221> NAME/KEY: MISC_FEATURE
<222> LOCATION: (4)..(6)
<223> OTHER INFORMATION: Xaa is any amino acid.

<400> SEQUENCE: 40

Xaa Xaa Xaa Xaa Xaa Xaa
1               5
```

ANTI-NEURODEGENERATIVE THERAPEUTIC, METHOD OF MANUFACTURE, AND USE

CROSS-REFERENCE TO RELATED APPLICATIONS

This application is a continuation-in-part of PCT/US2018/046491, filed Aug. 13, 2018, which claims priority to U.S. Provisional Application No. 62/544,046, filed Aug. 11, 2017, the entire disclosure of each of which is hereby incorporated by reference.

SEQUENCE STATEMENT

This application contains a Sequence Listing that has been submitted in ASCII format via EFS-Web and is hereby incorporated by reference in its entirety. The ASCII copy is named 085971-652927_Sequence_Listing_ST25.txt and is 10 kilobytes in size.

FIELD OF THE INVENTION

The invention relates to therapeutic peptides for the treatment and prevention of brain diseases, injuries, and disorders.

BACKGROUND

There continues to be a need for effective agents and methods for the treatment and prevention of brain diseases, injuries, and disorders that result in dopaminergic dysregulation. Current standards of treatment provide symptomatic relief of diseases, but do not prevent the progression of the disease. For example, levodopa provides symptomatic relief of Parkinson's disease, but does not halt the progression of neurodegeneration.

Many neurotrophic factors are both neuroprotective (protecting neurons from injury) and neurorestorative (promoting structural and/or functional regeneration). For example, glial cell-line derived neurotrophic factor (GDNF) is a neurotrophic factor shown to dramatically protect and enhance the function of dopamine neurons in vitro and in vivo in rodents and monkeys. However, clinical trials, involving ventricular delivery of GDNF showed no statistically significant differentiation of the placebo and active treatment groups, likely due to poor targeting of GDNF, as a result of poor biodistribution during site-specific delivery. Successful trophic factor therapy requires distribution throughout the target tissue, requiring site-specific delivery. The blood-brain barrier effectively blocks entry of large molecules from the blood stream, including trophic factors. Thus a useful drug for treating Parkinson's disease and other neurological injuries and disorders would possess neuroprotective and restorative actions using non-invasive delivery.

A crude peptide extract from the brain cerebrolysin has been tested in human studies, with modest effects reported (Lukhanina et al., 2004). Three small molecule compounds have also been tested in Parkinson's disease patients: the tripeptide glutathione, tocopherol, and Coenzyme Q10 (Weber et al., 2006). The three small molecule compounds have reportedly only minor benefits for patients. The amidated dopamine neuron stimulating peptide, DNSP-11 (an 11-amino acid peptide sequence), is described in U.S. Pat. Nos. 9,402,875, 9,586,992, and U.S. Ser. No. 12/646,511 (US Pub. No. 20110178025), U.S. Ser. No. 12/508,916 (US Pub. No. 20100035820), U.S. Ser. No. 15/193,605 filed Jun. 27, 2016, and U.S. Ser. No. 15/445,206 (US Pub. No. 20170173108) (all to Bradley et al.). The PAT nonapeptide (a 9-amino acid peptide sequence), is described in U.S. Ser. No. 14/929,449 to Laruelle et al., (US Pub. No. 20160074463). These peptides are distinguished by physical characteristics including size, charge, hydrophobicity rendering them and modified versions as agents that are often immunogenic.

A significant and common limitation for the use of peptides and proteins as therapeutics is the generation of antibody formation and other adverse effects (including toxicity) due to the activation of the immune system (Schellekens, 2010; Baker et al., 2010; Büttel et al., 2011; Leach et al., 2014; Rojko et al., 2014; Krishna & Nadler, 2016). For example, some patients reportedly developed an immune response following a clinical trial of recombinant human GDNF by intraputamenal CNS delivery (Lang et al., 2006; Tatarewicz et al., 2007). Human GDNF is a dimer that consists two identical 134 amino acid subunits. Other examples of antibody formation following therapeutic administration of recombinant proteins and peptides include Factor VIII (Prescott et al., 1997; Scharrer, 1999), imiglucerase (Brooks et al., 2003), beta-interferon (Durelli et al., 2004), erythropoietin (Casadevall et al., 2002), exenatide (Fineman et al., 2012), and intranasal-delivered insulin (Stoever et al., 2002). Factor VIII is reported to have 2332 amino acids, imiglucerase is reported to have 497 amino acids, beta-Interferon and erythropoietin are reported to have 165 amino acids, exenatide is reported to have 39 amino acids, and insulin is reported to have 51. In addition, these limitations apply to other large molecules such as monoclonal antibodies (full-length size approximately 150 kDa; Richards et al., 1999; Baert et al., 2002; Wagner et al., 2003; Bendtzen et al., 2006; Schmidt et al., 2009; Hansel et al., 2010) and their use to facilitate delivery and transport of recombinant proteins to the CNS. For example, the conjugation of the recombinant human GDNF sequence to a monoclonal antibody against the human insulin receptor to facilitate BBB transport has been reported to result in the generation of numerous adverse effects because of immune system activation (Oshima-Hosoyama et al., 2012).

The major histocompatibility complexes (MHC) play a critical selective role in the immune response. MHC are understood to recognize and bind peptide epitopes in the process of identifying non-self/foreign sequences and initiating an immune response by T-cells. There are two classes of MHCs, Class I (MHC-I) and Class II (MHC-II). Due to structural differences between MHC-I and MHC-II, there are size limitations of peptide sequences that are recognized and bound. MHC-I has a smaller binding pocket than MHC-II, preferentially binding peptides of 8-10 amino acids in length, with 9 amino acids being the most prevalent (MHC-II typically binding peptide sequences between 13-25 amino acids in length).

Providing therapeutic agents to the brain presents well known pharmacologic problems. Many of these center on the blood-brain barrier. The blood-brain barrier often described in the literature as a highly selective semipermeable membrane barrier that separates the circulating blood from the brain extracellular fluid in the central nervous system. Ventricular (brain) delivery and intraputamenal delivery of drugs has reportedly proven ineffective. Historically, brain drug therapy requires site-specific delivery and distribution of the therapeutic factor throughout the target tissue (the putamen for Parkinson's disease). The blood-brain barrier effectively blocks entry from blood borne proteins, including trophic factors. Without being bound by any particular, peptide infusions into the cerebrospinal fluid are not effective in humans because of brain size and may produce unwanted side effects by stimulating immune response cells such as sensory neurons.

Identifying and utilizing therapeutic candidates that "reach across" or bypass the blood-brain barrier or otherwise contact or enter brain tissue, with minimal immunogenicity, and treat Parkinson's disease, Alzheimer's disease, depression, Huntington's disease, prion disease, amyotrophic lateral sclerosis, a tauopathy, chronic traumatic encephalopathy, or other degenerative processes in the brain and central nervous system (including those induced by brain injury, stroke or cerebrovascular accident) is a recognized medical goal. Yet more expansively, breaching the blood-brain barrier is a therapeutic consideration in therapeutics treating epilepsy, depression, anxiety, PTSD, bipolar, psychiatric disorders.

SUMMARY OF THE INVENTION

The present disclosure provides a therapeutic peptide of the following sequence: $Xaa_1$-$Xaa_2$-$Xaa_3$-$Xaa_4$-$Xaa_5$ (SEQ ID NO: 39) and, optionally, $Xaa_6$ (SEQ ID NO: 40), wherein
$Xaa_1$, $Xaa_2$, $Xaa_4$, $Xaa_5$, and $Xaa_6$ each independently represent an amino acid;
$Xaa_3$ is proline; and wherein
subscripts represent the positions of each amino acid in the peptide sequence starting from the amino terminus of said peptide and extending to the C-terminus.

Therapeutic peptides disclosed herein are optionally cyclized with one or more linkers.

The present disclosure also provides a method of treating pathologies broadly understood to include neurodegenerative disorders, and associated conditions such as apathy, anxiety, depression, irritability and agitation in a human subject in need of such treatment by the process of administering to said subject a therapeutically effective amount of a therapeutic peptide disclosed herein.

In the therapeutic peptides disclosed herein, one or more of the amino acids may be deuterized and/or cyclized by the addition of terminal cysteines.

In the therapeutic peptides disclosed herein, $Xaa_1$ is an amino acid selected from the group consisting of leucine, tryptophan or glutamate.

In the therapeutic peptides disclosed herein, $Xaa_2$ is an amino acid selected from the group consisting of glycine, lysine, leucine, methionine, tryptophan or alanine.

In the therapeutic peptides disclosed herein, $Xaa_4$ is an amino acid selected from the group consisting of phenylalanine, lysine, leucine, tryptophan, tyrosine or alanine.

In the therapeutic peptides disclosed herein, $Xaa_5$ is an amino acid selected from the group consisting of alanine, cysteine, aspartate, leucine, methionine, asparagine, serine or glutamate.

Particular reference is made to $Xaa_6$ which is an amino acid selected from the group consisting of alanine, cysteine, glutamate, phenylalanine, glycine, leucine, proline, serine, or aspartate.

In some aspects, one or more amino acid is a D-amino acid.

In a therapeutic peptide as disclosed herein, the C-terminus of the therapeutic peptide further optionally includes amidation.

In a therapeutic peptide as disclosed herein, the N-terminus of the therapeutic peptide further optionally includes acylation.

The therapeutic peptides may further comprise two or more peptides, optionally further comprising an adjunct.

The disclosed therapeutic peptides further usefully comprise a pharmaceutically acceptable carrier and/or excipient.

The present disclosure also provides a method of treating a neurodegenerative disorder in a human subject in need of such treatment by the process of administering to said subject a therapeutically effective amount of a therapeutic peptide of the following sequence: $Xaa_1$-$Xaa_2$-$Xaa_3$-$Xaa_4$-$Xaa_5$ (SEQ ID NO: 39) wherein $Xaa_1$, $Xaa_2$, $Xaa_4$, and $Xaa_5$, each independently represent an amino acid, $Xaa_3$ is proline; and, subscripts represent the positions of each amino acid in the peptide sequence starting from the amino terminus of said peptide extending to the C-terminus, and optionally further comprising -$Xaa_6$ (SEQ ID NO: 40) wherein $Xaa_6$ represents an amino acid.

The therapeutic peptides disclosed herein are usefully administered at: (i) from about 0.1 to about 1000 mgs. with particular reference to 1 to 100 mgs; and (ii) from about twice daily to about weekly/monthly for two weeks, five years, chronically Delivery of the claimed therapeutic peptides disclosed herein is broadly understood to include any systemic route of administration, such as intranasal, sublingual, buccal, intraocular, intraperitoneal, intrapulmonary, rectal, intramuscular, intradermal, transdermal, subcutaneous, or intravenous administration, with particular emphasis on intranasal and subcutaneous administration.

In some aspects, one or more amino acid is a D-amino acid.

BRIEF DESCRIPTION OF THE DRAWINGS

FIG. 1A: Tissue DA levels (ng/g—wet tissue weight) from the entire striatum (both hemispheres) of normal Fischer 344 rats intranasally administered with 50 microliters total of vehicle or AV6403 (1.1 mg/mL or 3.5 mg/mL), 5 days a week for 3 weeks. All data were analyzed by one-way ANOVA ($*p<0.05$) and are presented as a mean±SEM, N=12 for vehicle and each AV6403 treatment group.

FIG. 1B: Tissue DOPAC levels (ng/g—wet tissue weight) from the entire striatum (both hemispheres) of normal Fischer 344 rats intranasally administered with 50 microliters total of vehicle or AV6403 (1.1 mg/mL or 3.5 mg/mL), 5 days a week for 3 weeks. All data were analyzed by one-way ANOVA ($*p<0.05$) and are presented as a mean±SEM, N=12 for vehicle and each AV6403 treatment group.

FIG. 1C: Tissue HVA levels (ng/g—wet tissue weight) from the entire striatum (both hemispheres) of normal Fischer 344 rats intranasally administered with 50 microliters total of vehicle or AV6403 (1.1 mg/mL or 3.5 mg/mL), 5 days a week for 3 weeks. All data were analyzed by one-way ANOVA ($*p<0.05$) and are presented as a mean±SEM, N=12 for vehicle and each AV6403 treatment group.

FIG. 6A: Tissue DA levels (ng/g—wet tissue weight) from the entire striatum (both hemispheres) of normal Fischer 344 rats intranasally administered with 50 microliters total of vehicle or AV7624 (1.2 mg/mL or 3.6 mg/mL), 5 days a week for 3 weeks. All data were analyzed by one-way ANOVA with Tukey's multiple comparisons test (**p<0.01), Brown-Forsythe test (+++p<0.001), or Bartlett's test (##p<0.01) post hoc analysis, and are presented as a mean±SEM, N=12 for vehicle and each AV7624 treatment group.

FIG. 6B: Tissue DOPAC levels (ng/g—wet tissue weight) from the entire striatum (both hemispheres) of normal Fischer 344 rats intranasally administered with 50 microliters total of vehicle or AV7624 (1.2 mg/mL or 3.6 mg/mL), 5 days a week for 3 weeks. All data were analyzed by one-way ANOVA with Tukey's multiple comparisons test (**p<0.01), Brown-Forsythe test (+++p<0.001), or Bartlett's test (##p<0.01) post hoc analysis, and are presented as a mean±SEM, N=12 for vehicle and each AV7624 treatment group.

FIG. 6C: Tissue HVA levels (ng/g—wet tissue weight) from the entire striatum (both hemispheres) of normal Fischer 344 rats intranasally administered with 50 microliters total of vehicle or AV7624 (1.2 mg/mL or 3.6 mg/mL), 5 days a week for 3 weeks. All data were analyzed by one-way ANOVA with Tukey's multiple comparisons test (**p<0.01), Brown-Forsythe test (+++p<0.001), or Bartlett's test (##p<0.01) post hoc analysis, and are presented as a mean±SEM, N=12 for vehicle and each AV7624 treatment group.

FIG. 7A: DA turnover ratios (DOPAC/DA) of the whole striatum (both hemispheres) of normal Fischer 344 intranasally administered with 50 microliters total of vehicle or AV7624 (1.2 mg/mL or 3.6 mg/mL), 5 days a week for 3 weeks. All data were analyzed by one-way ANOVA with Tukey's post hoc analysis (*p<0.05) and are presented as a mean±SEM, N=12 for vehicle and each AV7624 treatment group.

FIG. 7B: DA turnover ratios ([HVA+DOPAC]/DA) of the whole striatum (both hemispheres) of normal Fischer 344 intranasally administered with 50 microliters total of vehicle or AV7624 (1.2 mg/mL or 3.6 mg/mL), 5 days a week for 3 weeks. All data were analyzed by one-way ANOVA with Tukey's post hoc analysis (*p<0.05) and are presented as a mean±SEM, N=12 for vehicle and each AV7624 treatment group.

FIG. 8A: Tissue 5-HT levels (ng/g—wet tissue weight) from the entire striatum (both hemispheres) of normal Fischer 344 rats intranasally administered with 50 microliters total of vehicle or AV7624 (1.2 mg/mL or 3.6 mg/mL), 5 days a week for 3 weeks. All data were analyzed by one-way ANOVA with Dunnett's multiple comparison test (*p<0.05, **p<0.01) and are presented as a mean±SEM, N=12 for vehicle and each AV7624 treatment group.

FIG. 8B: Tissue 5-HIAA levels (ng/g—wet tissue weight) from the entire striatum (both hemispheres) of normal Fischer 344 rats intranasally administered with 50 microliters total of vehicle or AV7624 (1.2 mg/mL or 3.6 mg/mL), 5 days a week for 3 weeks. All data were analyzed by one-way ANOVA with Dunnett's multiple comparison test (*p<0.05, **p<0.01) and are presented as a mean±SEM, N=12 for vehicle and each AV7624 treatment group.

DETAILED DESCRIPTION

Figure 2A:
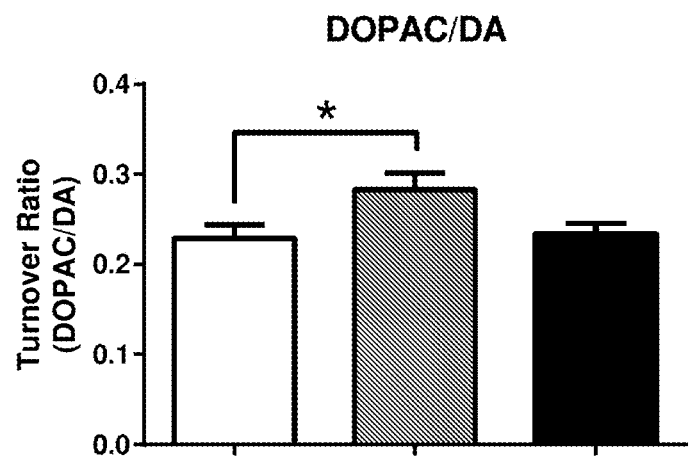
FIG. 2A: DA turnover ratios (DOPAC/DA) of the whole striatum (both hemispheres) of normal Fischer 344 intranasally administered with 50 microliters total of vehicle or AV6403 (1.1 mg/mL or 3.5 mg/mL), 5 days a week for 3 weeks. All data were analyzed by one-way ANOVA ($*p<0.05$) and are presented as a mean±SEM, N=12 for vehicle and each AV6403 treatment group.

The present disclosure presents active peptide molecules of less than eight (8) amino acids in length, and particularly peptide molecules of five (5) and six (6) amino acids in length. These peptides exhibit significantly less immunogenicity and engender far diminished related adverse effects.

This disclosure will best be understood with reference to the following definitions:

A. "Amino acid" or amino acids shall mean all known naturally occurring or synthetic amino acids. Particular note is made of the chirality of amino acids. Both D and L forms of amino acids are contemplated within this invention.

B. "Deuterated" or deuterized shall mean an amino acid of a peptide of this invention wherein one or more of the hydrogen atoms contained in the peptide have been replaced by deuterium. Without being bound by any particular theory, it is believed that because of the kinetic isotope effect, deuterium-containing peptides may have significantly lower rates of metabolism, and hence a longer half-life upon administration to a subject. Deuterated amino acids are generally available (e.g., Sigma-Aldrich, Cambridge Isotope Laboratories, Inc.).

C. "Cyclized" or cyclic peptides (or cyclic proteins) shall mean polypeptide chains in which the amino termini and carboxyl termini are linked with a covalent bond that generates a ring. In the present invention the disclosed 5 and 6 amino peptides may be advantageously cyclized by the addition of a cysteine at each end of the peptide. Peptides of the invention are, when cyclized, 5+2 Cys or 6+2 Cys. Multiple useful linkers are known in the art and included herein.

D. "Adjunct" as used herein shall be broadly understood to mean modifications that facilitate marking the peptide for detection, while maintaining biological activity. Contemplated adjuncts include without limitation radio-isotopes, photo-affinity ligands, and fluorescent compounds.

E. "Systemic" administration can be any route of administration capable of delivering a substance into the circulatory system. Non-limiting examples of routes of systemic administration include parenteral, enteral, or topical administration such as intranasal, sublingual, buccal, intraocular, intraperitoneal, intrapulmonary, rectal, intradermal, transdermal, subcutaneous, intramuscular, or intravenous administration. "Intranasal" or intranasally administering a therapeutic includes administering the therapeutic to a nasal passage (e.g., the epithelium of the nasal cavity, the epithelium of the upper nasal cavity, the superior nasal concha). Intranasal administration can be in the form of an aerosol, or an intranasal lavage. Dry-powder sprays are also contemplated.

F. As used herein, "traumatic brain injury" (TBI) refers to a form of acquired brain injury that occurs when a sudden trauma causes brain damage. TBI can occur when the head suddenly and violently hits an object, or when an object pierces the skull and enters brain tissue. TBI symptoms can be mild, moderate, or severe, depending on the extent of the damage to the brain.

G. As a matter of terminology economy, "crossing the blood-brain barrier" shall be broadly understood to encompass drugs being made available to interact with brain (or other CNS) tissue. Crossing the blood-brain barrier includes a drug which "reaches across" or bypasses the blood-brain barrier or otherwise is placed in contact with or enters brain tissue. Without being bound by any particular mechanism, literature reports also cite as crossing the blood-brain barrier water, some gases, and lipid-soluble molecules by passive diffusion, as well as the selective transport of molecules such as glucose and amino acids.

H. TBI Gradation: Although the terms "mild," "moderate," or "severe" can be applied arbitrarily, generally, "mild" traumatic brain injury refers to a traumatic brain injury that results in loss of consciousness for a few seconds to a few minutes; no loss of consciousness, but a dazed, confused or disoriented state; headache; nausea or vomiting; fatigue or drowsiness; difficulty sleeping; sleeping more than usual; and/or dizziness or loss of balance. The mild traumatic brain injury can also create blurred vision; ringing in the ears; a bad taste in the mouth or changes in the ability to smell; and/or sensitivity to light or sound. Cognitive or mental symptoms of mild traumatic brain injury include memory or concentration problems; mood changes or mood swings; and/or feeling depressed or anxious. "Moderate" or "severe" traumatic brain injury refers to a traumatic brain injury that results in loss of consciousness from several minutes to hours; persistent headache or headache that worsens; repeated vomiting or nausea; convulsions or seizures; dilation of one or both pupils of the eyes; clear fluids draining from the nose or ears; inability to awaken from sleep; weakness or numbness in fingers and toes; and/or loss of coordination. Cognitive and mental symptoms include profound confusion; agitation; combativeness or other unusual behavior; slurred speech; coma and/or other disorders of consciousness.

I. AV6403 shall mean the peptide Leu-Ala-Pro-Ala-Glu-Asp-$NH_2$. (SEQ ID NO: 1)

J. AV7624 shall mean the peptide Glu-Ala-Pro-Phe-Glu-Asp-$NH_2$. (SEQ ID NO: 2)

K. AV2387 shall mean the peptide Leu-Ala-Pro-Tyr-Glu-Asp-$NH_2$. (SEQ ID NO: 3)

The following abbreviations are noted:
5-HIAA—5-hydroxyindoleacetic acid;
5-HT or serotonin—5-hydroxytryptamine;
Accumbens—' nucleus accumbens;
Caudate—Caudate nucleus;
CTX—frontal cortex;
CXT—motor cortex;
DA—Dopamine;
DOPAC—3,4-Dihydroxy-Phenylacetic Acid (DOPAC);
GP—globus pallidus.
HVA—Homovanillic Acid;
MPP+—1-methyl-4-phenylpyridinium
NE—norepinephrine
Occipital CTX—occipital cortex
RP-HPLC EC—Reverse-Phase High Pressure Liquid Chromatography Electrochemical detection;
SN—substantia nigra;
TaClo—trichloromethyl-1,2,3,4-tetrahydro-β-carboline.

The present invention is based on the discovery of compositions and methods that are useful in treating neurodegenerative and neurological disorders. Neurodegenerative disorders encompassed by the invention include those of the motor system (e.g., Parkinson's disease), as well as other neurological syndromes such as Alzheimer's, TBI, prion disease, amyotrophic lateral sclerosis, tauopathy, chronic traumatic encephalopathy, or other degenerative processes in the brain and central nervous system (including those induced by brain injury, stroke or cerebrovascular accident), and Huntington's diseases. Further included are those neurodegenerative and neurological disorders which, without being bound by any particular theory, are thought to be associated with altered biogenic amine (e.g., dopamine) neurotransmitter levels (including depression, anxiety, bipolar disorder, post-traumatic stress disorder) and yet further pathologies associated with neuronal dysregulations. Note is yet further made of neurodegenerative conditions associated with reperfusion injury.

The present invention focused on selecting therapeutically effective peptide sequences that were non-immuno-genic. Disclosed are sequences of six amino acids or smaller. The Immune Epitope Database and Analysis Resource (IEDB; accessible at iedb.org; Kim et al., 2012), lists 328,089 linear immunogenic peptide epitopes that yield a positive T-cell, B-cell, or MHC-ligand assay response in a range of hosts (including humans). Our analysis found that 306,355 (93.4%) of all listed epitopes were 9 amino acids or longer in length. Only 2,714 out of 328,089 listed linear positive epitopes (or 0.8%) are six amino acids in length or less.

Discovery of the instant sequence identities that are substantially non-immunogenic was the result of examining over 150 C-terminal amidated peptide sequences. Testing involved permutations of size and diversifying amino acid sequence at each residue position. Sequence design began with Proline-Proline-Glutamate-Alanine-Proline-Alanine-Glutamate-Aspartate-Arginine-Serine-Leucine-NH2. This sequence was used as a starting point to identify smaller substantially non-immunogenic peptide sequences that were both non-toxic and neuroprotective against neurotoxins. These properties were tested using the dopaminergic MN9D neuronal cell line. Each candidate peptide sequence was dissolved in citrate buffer and added to MN9D cells (Choi et al., 1992) that were cultured in Dulbecco's Modified Eagle's Medium [DMEM (containing pyridoxol HCl); Sigma, St. Louis, MO] supplemented with 10% Fetal Bovine serum (HyClone, Logan, UT), 50 U/ml penicillin and streptomycin to a final 100 nM concentration. Using LIVE/DEAD and JC-1 assays in MN9D neuronal cells, individual library sequences were measured for toxicity and loss of mitochondrial potentials at 1 and 3 hours post treatment. At 100 nM concentrations, most amino acid substitutions at position 3 and 5 (of the starting 11 amino acid sequence, glutamate and proline respectively) resulted in an increase in toxicity and significant loss of mitochondrial potentials at 1 h. In addition, peptides smaller than 5 amino acids resulted in an increase in toxicity and significant loss of mitochondrial potentials at 1 h. The remaining sequences were then tested for their ability to provide protection against neurotoxins rotenone, 1-methyl-4-phenylpyridinium (MPP+), and trichloromethyl-1,2,3,4-tetrahydro-β-carboline (TaClo). Selecting a 100 nM dosage, pretreatment of library members provided significant protection of MN9D neuronal cells mitochondrial potentials against predetermined concentrations of rotenone, MPP+, and TaClo-induced cytotoxicity at different time points (1, 3, 12, 24 hours). Of the remaining 120 sequences tested, the 5 (and 6) amino acid fragments Glutamate-Alanine-Proline-Alanine-Glutamate-NH2 (SEQ ID NO: 10) and Glutamate-Alanine-Proline-Alanine-Glutamate-Aspartate-NH2 (SEQ ID NO: 11) were the shortest fragments to provide both low toxicity and protection against neurotoxin exposure at all time points measured. Twenty-seven positional variants of this fragment were then identified as also exhibiting minimal toxicity and significant protection against neurotoxins at all time points tested.

The therapeutic peptides of this invention particularly include 5- or 6-mer amino acid peptides of the following sequence:

$Xaa_1$-$Xaa_2$-$Xaa_3$-$Xaa_4$-$Xaa_5$ (SEQ ID NO: 39) and optionally -$Xaa_6$ (SEQ ID NO: 40)
  wherein
  $Xaa_1$, $Xaa_2$, $Xaa_4$, $Xaa_5$, and $Xaa_6$ each independently represent an amino acid $Xaa_3$ is proline and,
  subscripts represent the positions of each amino acid in the peptide sequence starting from the amino terminus of said peptide extending to the C-terminus.

Through exhaustive study the disclosed peptides are the minimum effective size to accomplish the therapeutic purpose. The following permutations are noted, (e.g., SEQ ID NO: 12 and SEQ ID NO: 13):

$Xaa_1$ can be any of leucine, tryptophan or glutamate.

$Xaa_2$ can be any of glycine, lysine, leucine, methionine, tryptophan or alanine.

$Xaa_3$ is proline in each instance.

$Xaa_4$ can be phenylalanine, lysine, leucine, tryptophan, tyrosine or alanine.

$Xaa_5$ can be alanine, cysteine, aspartate, leucine, methionine, asparagine, serine or glutamate.

$Xaa_6$, if present, can be alanine, cysteine, glutamate, phenylalanine, glycine, leucine, proline, serine, or aspartate.

The C-terminus of the 5 or 6 mer peptide can be amidated. In addition, the 5 or 6 mer peptide may be cyclized such as by the addition of cysteine at the termini.

Any one or more of the amino acids of the therapeutic peptides can be achiral (i.e., glycine), or D or L. Any one or more of the amino acids can be deuterized or cyclized.

In one embodiment, and taking advantage of the ability of the disclosed peptides to enter the CNS, the peptides may also be linked to or associated with adjuncts, such as adjuncts radio-isotopes, photo-affinity ligands, fluorescent compounds, antibodies, and small molecules.

Additionally contemplated are modifications of the N and C-termini of a peptide. Without limitation, these modifications include: acetylation, amidation, lipoic acids, palmitic acids, phosphorylation, polyethylene glycol (PEG), and succinylations to improve stability and bioavailability, cell permeability, efficacy, and conjugation.

The therapeutic peptides of this invention are usefully administered at: (i) from about 0.1 to about 1000 mgs, with particular reference to 1 to 100 mgs; (ii) from about twice daily to about weekly/monthly for two weeks, five years, chronically; (iii) intranasal, sublingual, subcutaneous, and buccal doses are particularly noted.

Particular note is made of intranasal, sublingual, subcutaneous, and buccal administration of the substances disclosed herein.

EXAMPLES

The publications discussed above are provided solely for their disclosure before the filing date of the present application. Nothing herein is to be construed as an admission that the invention is not entitled to antedate such disclosure by virtue of prior invention.

The following examples are included to demonstrate the disclosure. It should be appreciated by those of skill in the art that the techniques disclosed in the following examples represent techniques discovered by the inventors to function well in the practice of the disclosure. Those of skill in the art should, however, in light of the present disclosure, appreciate that many changes could be made in the disclosure and still obtain a like or similar result without departing from the spirit and scope of the disclosure, therefore all matter set forth is to be interpreted as illustrative and not in a limiting sense.

Example 1

Leucine-Glycine-Proline-Phenylalanine-Serine-Glutamate (SEQ ID NO: 4) Treating Alzheimer's Disease A 78 year old male presents with—mild cognitive impairment Alzheimer's disease. He is intranasally administered 5 mg at once per day for 360 days. At 1, 90, 180, 270 and 360 days he is tested/retested with a battery of cognitive tests including Alzheimer's Disease Assessment Scale-Cognitive Subscale Test (ASAS-Cog Test), Alzheimer's Disease Assessment Scale—plus executive function (EF) and functional abilities (FA) (ADAS-Cog-plus), Clock Drawing Interpretation Scale (CDIS), Dementia Rating Scale, Global Deterioration Scale, Mini-Mental State Exam (MMSE), Alzheimer's Disease Cooperative Study-Activities of Daily Living (ADCS-ADL), Clinical Dementia Rating (CDR). He exhibits minimal to no cognitive loss from day 1 over 360 days.

Example 2

Leucine-Glycine-Proline-Phenylalanine-Serine-Glutamate-$NH_2$ (SEQ ID NO: 4) Treating TBI A 43 year old female presents with moderate loss of cognition from clinical diagnosis of traumatic brain injury using the National Institute of Neurological Disorders and Stroke TBI Common Data Elements definition based on head injury in a fall. She is intranasally administered 1 mg at 4 times per day for 45 days. At 1, 90, 180, 270 and 360 days she is tested/retested with a battery of cognitive tests Hopkins Verbal Learning Test-Revised (HVLT-R), Trail Making Test Parts A and B, the Wechsler Adult Intelligence Scale-IV (WAIS-IV) Digit Span, Barthel Index, modified Rankin Scale, Glasgow Outcome Scale. She shows minimal to no additional cognitive loss from day 1 over 360 days.

Example 3

Cyclo (cys-Leucine-Glycine-Proline-Phenylalanine-Serine-Glutamate-cys (SEQ ID NO: 5) Treating Parkinson's Disease A 62 year old male presents with current diagnosis of Parkinson's disease with motor complications and responsiveness to levodopa or dopa agonists. He is buccally administered 100 mg at every 12 hours for 180 days. At 1, 90, 180, 270 and 360 days he is tested/retested with a battery of neurological tests including Unified Parkinson's Disease Rating Scale (UPDRS), Time Tests, Hoehn and Yahr (HY) Scale, Clinical Global Impression of Severity (CGIS), Clinical Impression of Severity Index (CISI-PD), Patient Global Impression of Severity (PGIS). He exhibits minimal to no additional test loss from day 1 over 360 days.

Example 4

Tryptophan-D-Alanine-Proline-D-Lysine-Asparagine-$NH_2$ (SEQ ID NO: 6) Treating Alzheimer's Disease A 73 year old female presents with diagnosis of Alzheimer's disease. She is intranasally administered 100 mg once a week for 30 days. At 1, 90, 180, 270 and 360 days she is tested/retested with a battery of cognitive tests including Alzheimer's Disease Assessment Scale-Cognitive Subscale Test (ASAS-Cog Test), Alzheimer's Disease Assessment Scale—plus executive function (EF) and functional abilities (FA) (ADAS-Cog-plus), Clock Drawing Interpretation Scale (CDIS), Dementia Rating Scale, Global Deterioration Scale, Mini-Mental State Exam (MMSE), Alzheimer's Disease Cooperative Study-Activities of Daily Living (ADCS-ADL), Clinical Dementia Rating (CDR). She exhibits minimal to no cognitive loss from day 1 over 360 days.

Example 5

D-Glutamate-Alanine-Proline-Phenylalanine-D-Alanine-Glycine-$NH_2$(SEQ ID NO: 7) Treating Alzheimer's Disease A 66 year old female presents with diagnosis of Alzheimer's Disease. She is buccally administered 25 mg daily for 60 days. At 1, 90, 180, 270 and 360 days she is tested/retested with a battery of cognitive tests including Alzheimer's Disease Assessment Scale-Cognitive Subscale Test (ASAS-Cog Test), Alzheimer's Disease Assessment Scale—plus executive function (EF) and functional abilities (FA) (ADAS-Cog-plus), Clock Drawing Interpretation Scale (CDIS), Dementia Rating Scale, Global Deterioration Scale, Mini-Mental State Exam (MMSE), Alzheimer's Disease Cooperative Study-Activities of Daily Living (ADCS-ADL), Clinical Dementia Rating (CDR). She exhibits minimal to no cognitive loss from day 1 over 360 days.

Example 6

Glutamate-deuterated Lysine-Proline-D-Phenylalanine-deuterated Leucine-$NH_2$ (SEQ ID NO: 8) Treating Parkinson's Disease A 51 year old female presents with diagnosis of Parkinson's disease. She is administered peptide by intranasal spray at a dosage of 25 mg, daily for 60 days. At 1, 90, 180, 270 and 360 days she is tested/retested with a battery of neurological tests including Unified Parkinson's Disease Rating Scale (UPDRS), Time Tests, Hoehn and Yahr (HY) Scale, Clinical Global Impression of Severity (CGIS), Clinical Impression of Severity Index (CISI-PD), Patient Global Impression of Severity (PGIS). She exhibits minimal to no additional UPDRS loss from day 1 over 360 days.

Example 7

Ac-Leucine-D-Methionine-Proline-Alanine-deuterated Serine-Phenylalanine (SEQ ID NO: 9) Treating Depression A 48 year old female presents with the diagnosis of depression. She is administered peptide by intranasal spray at a dosage of 50 mg daily for 270 days. At 1, 90, 180, 270 and 360 days she is tested/retested with a battery of mental status tests including Hamilton Depression Scale (HAMD), Mini Mental Status Exam (MMSE), Beck Depression Index (BDI), Montgomery-Asberg Depression Rating Scale (MADRS), Clinical Global Impression Scale (CGI), Patient Global Impression Scale (PGI), Structural Clinical Interview for Diagnostic and Statistic Manual of Mental Disorders IV (SCID). The patient exhibits improvement in HAMD from day 1 over 360 days.

Example 8

Leucine-Alanine-Proline-Alanine-Glutamate-Aspartate-$NH_2$ (SEQ ID NO: 1) Effects on Neurochemistry of the Striatum and Substantia Nigra All animal procedures were conducted in the Laboratory Animal Facilities of the University of Kentucky and approved by the University of Kentucky Institutional Animal Care and Use Committee in agreement with the Association for Assessment and Accreditation of Laboratory Animal Care (AAALAC) guidelines.

Groups of 12, 3 month old Fischer 344 rats were intranasally dosed 50 microliters (4 single 12.5 microliter administrations, 2 per nare, 5 minutes between each nare administration) of either vehicle, 1.1 mg/mL, or 3.5 mg/mL of AV6403 [Leu-Ala-Pro-Ala-Glu-Asp-$NH_2$] (SEQ ID NO: 1) once a day for 5 days a week, for 3 weeks (5 consecutive days of dosing, 2 off days, repeated total of 3 times). Following day 21, rats were euthanized and brain tissue was recovered and sections removed and weighed for neurochemical analysis by Reverse-Phase High Pressure Liquid Chromatography Electrochemical detection (RP-HPLC EC).

Figure 2B:
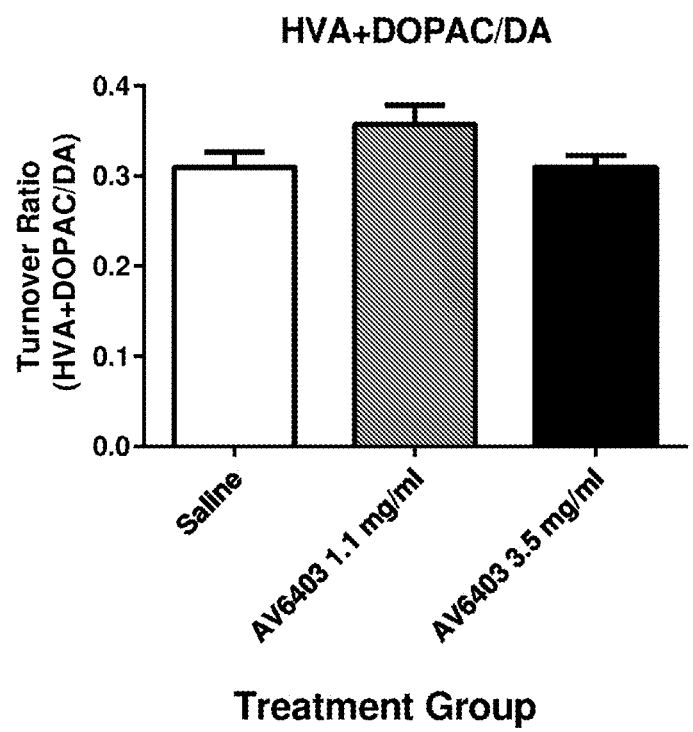
FIG. 2B: DA turnover ratios ([HVA+DOPAC]/DA) of the whole striatum (both hemispheres) of normal Fischer 344 intranasally administered with 50 microliters total of vehicle or AV6403 (1.1 mg/mL or 3.5 mg/mL), 5 days a week for 3 weeks. All data were analyzed by one-way ANOVA (*p<0.05) and are presented as a mean±SEM, N=12 for vehicle and each AV6403 treatment group.
Figure 3:
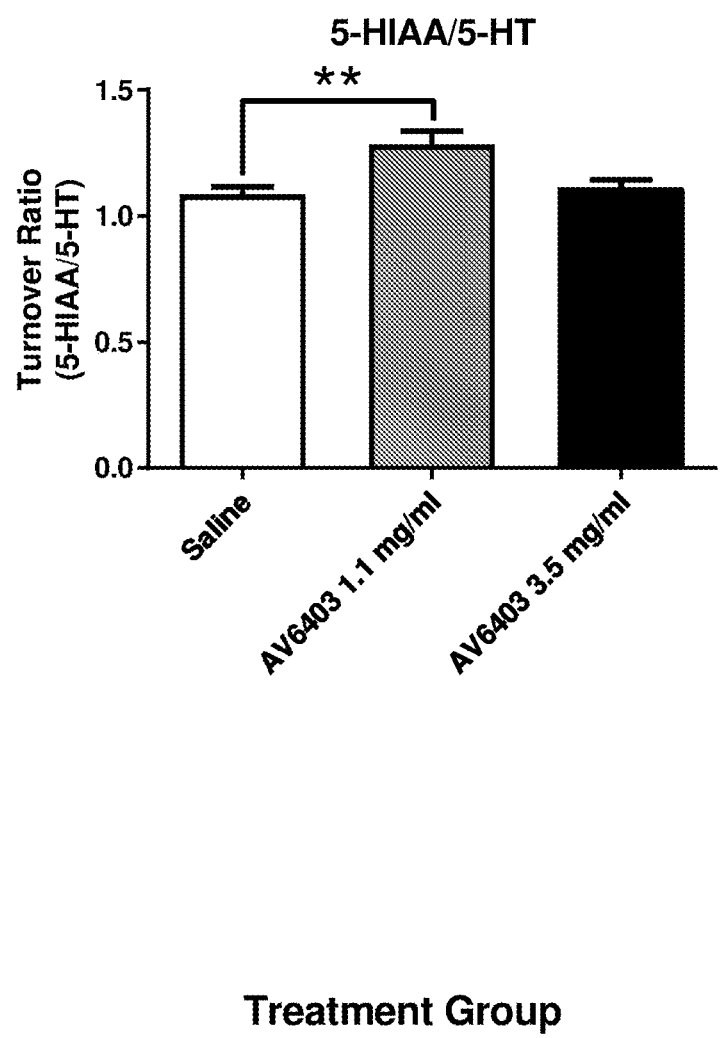
FIG. 3: 5-HT turnover ratio of the whole striatum (both hemispheres) of normal Fischer 344 intranasally administered with 50 microliters total of vehicle or AV6403 (1.1 mg/mL or 3.5 mg/mL), 5 days a week for 3 weeks. All data were analyzed by one-way ANOVA with Dunnett's multiple comparison test (**p<0.05) and are presented as a mean±SEM, N=12 for vehicle and each AV6403 treatment group.

Dopamine [DA], its major metabolites 3,4-Dihydroxy-Phenylacetic Acid (DOPAC) and Homovanillic Acid (HVA), 5-hydroxytryptamine (5-HT, serotonin), its metabolite 5-hydroxyindoleacetic acid (5-HIAA), and norepinephrine (NE) were measured in the striatum and substantia nigra (SN) for each group. In the striatum [TABLE 1], 1.1 mg/mL dosing of AV6403 led to a 20% and 25% reduction of DA and HVA levels [FIG. 1A-FIG. 1C], respectively, resulting in an increase in dopamine turnover (22% [DOPAC/DA] and 16% [[(HVA+DOPAC)/DA]), relative to saline vehicle treated rats [FIG. 2A-FIG. 2B]. The higher 3.5 mg/mL dosage of AV6403 resulted in slight increases of striatal DA and DOPAC (8% and 11%) levels and minor changes in DA turnover [FIG. 1A-FIG. 1C, FIG. 2A-FIG. 2B]. Repeated intranasal treatment with 1.1 mg/mL AV6403 resulted in about a 32% and 19% reduction of 5-HT and 5-HIAA and an 19% increase in turnover [5-HIAA/5-HT, FIG. 3] whereas the higher AV6403 dosage resulted in small increases, relative to saline treated rats [TABLE 2]. NE levels were reduced in the striatum with about a 36% reduction for AV6403 1.1 mg/mL dosage versus vehicle [TABLE 1].

Figure 4A:
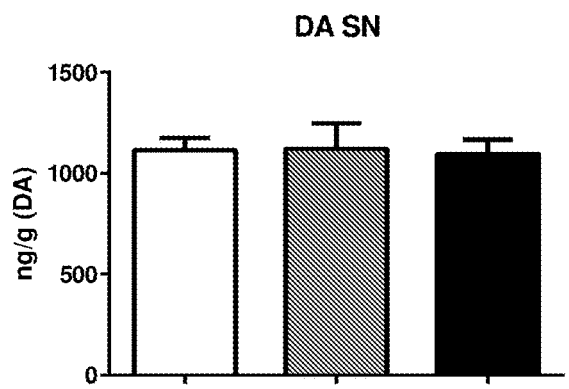
FIG. 4A: Tissue DOPAC levels (ng/g—wet tissue weight) from the entire substantia nigra (both hemispheres) of normal Fischer 344 rats intranasally administered with 50 microliters total of vehicle or AV6403 (1.1 mg/mL or 3.5 mg/mL), 5 days a week for 3 weeks. All data were analyzed by one-way ANOVA (*p<0.05) and are presented as a mean±SEM, N=12 for vehicle and each AV6403 treatment group.
Figure 4B:
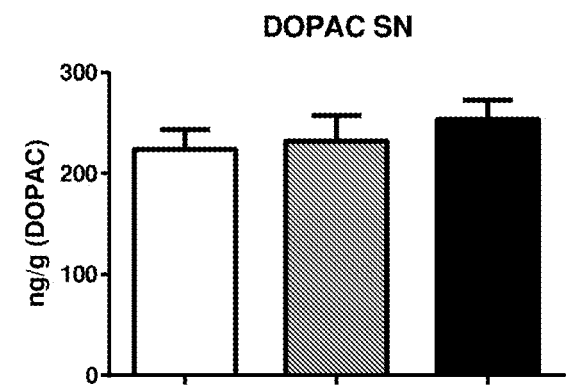
FIG. 4B: Tissue DOPAC levels (ng/g—wet tissue weight) from the entire substantia nigra (both hemispheres) of normal Fischer 344 rats intranasally administered with 50 microliters total of vehicle or AV6403 (1.1 mg/mL or 3.5 mg/mL), 5 days a week for 3 weeks. All data were analyzed by one-way ANOVA (*p<0.05) and are presented as a mean±SEM, N=12 for vehicle and each AV6403 treatment group.
Figure 4C:
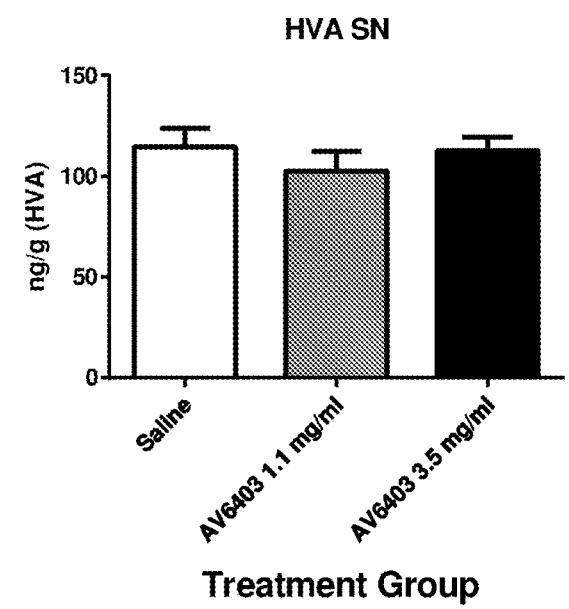
FIG. 4C: Tissue HVA levels (ng/g—wet tissue weight) from the entire substantia nigra (both hemispheres) of normal Fischer 344 rats intranasally administered with 50 microliters total of vehicle or AV6403 (1.1 mg/mL or 3.5 mg/mL), 5 days a week for 3 weeks. All data were analyzed by one-way ANOVA (*p<0.05) and are presented as a mean±SEM, N=12 for vehicle and each AV6403 treatment group.
Figure 5A:
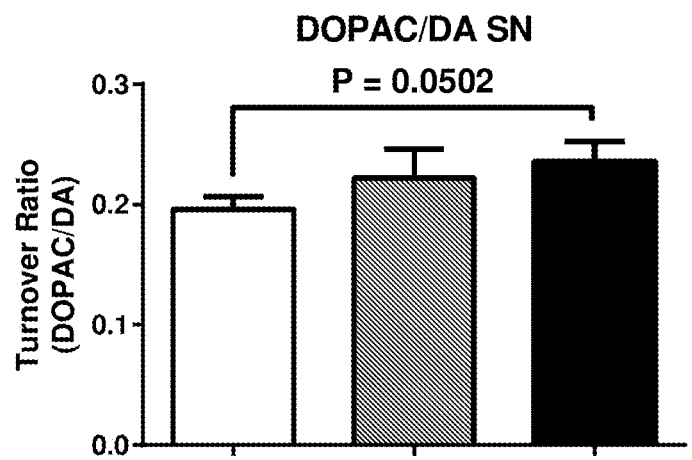
FIG. 5A: DA turnover ratios (DOPAC/DA) of the whole substantia nigra (both hemispheres) of normal Fischer 344 intranasally administered with 50 microliters total of vehicle or AV6403 (1.1 mg/mL or 3.5 mg/mL), 5 days a week for 3 weeks. All data were analyzed by one-way ANOVA with unpaired T-Test (*p<0.05) and are presented as a mean±SEM, N=12 for vehicle and each AV6403 treatment group.
Figure 5B:
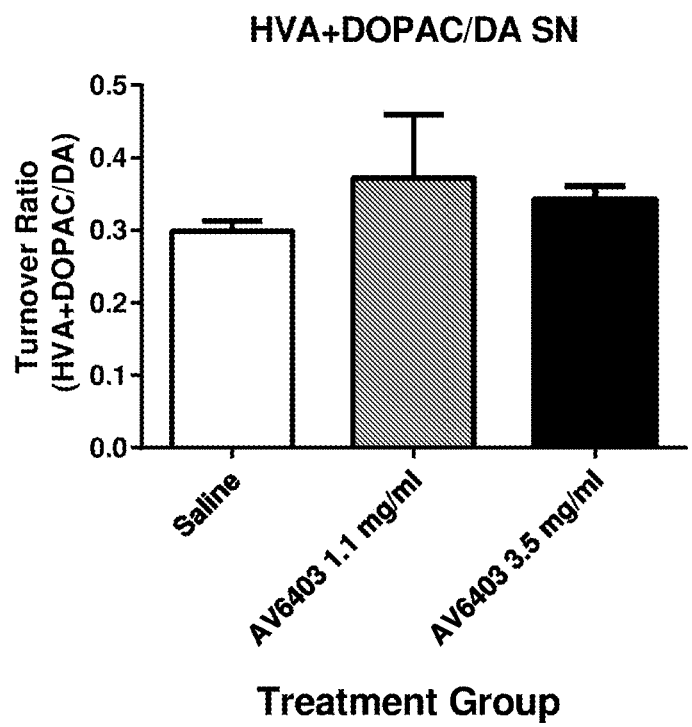
FIG. 5B: DA turnover ratios ([HVA+DOPAC]/DA) of the whole substantia nigra (both hemispheres) of normal Fischer 344 intranasally administered with 50 microliters total of vehicle or AV6403 (1.1 mg/mL or 3.5 mg/mL), 5 days a week for 3 weeks. All data were analyzed by one-way ANOVA with unpaired T-Test (*p<0.05) and are presented as a mean±SEM, N=12 for vehicle and each AV6403 treatment group.

In the SN [TABLE 3], treatment of AV6403 led to about a 13% increase in DOPAC and a 11% reduction of HVA, depending on the dosage, [FIG. 4A-FIG. 4C] resulting in an increase in dopamine turnover (20% [DOPAC/DA] for 3.5 mg/mL dosage; 23% [(HVA+DOPAC)/DA] for 1.1 mg/mL) relative to saline vehicle treated rats [FIG. 5A-FIG. 5B]. Treatment with 1.1 mg/mL AV6403 decreased 5-HT by 10% in the SN, resulting in a 16% increase in serotonin turnover [5-HIAA/5-HT] [TABLE 4]. The higher dosage (3.5 mg/mL AV6403) increased NE levels in the SN by about 23% versus vehicle treated rats, respectively [TABLE 3].

TABLE 1

TABLE 1: Striatum levels (ng/g - wet tissue weight) in normal Fischer 344 rats of DA, DOPAC, HVA, 5-HT, 5-HIAA, and NE following repeated intranasal administration of AV6403.

AV6403 Combined Left and Right Striatum ng/g

| TA Code | | DA | DOPAC | HVA | 5-HT | 5-HIAA | NE |
|---|---|---|---|---|---|---|---|
| Saline | Mean | 11546 | 2620 | 941 | 376 | 403 | 70 |
| | (+/−)SEM | 461 | 187 | 49 | 20 | 22 | 8 |
| | N | 12 | 12 | 12 | 12 | 12 | 12 |
| AV6403 1.1 mg/ml | Mean | 9425 | 2618 | 699 | 257 | 326 | 45 |
| | (+/−)SEM | 743 | 239 | 52 | 14 | 20 | 5 |
| | N | 12 | 12 | 12 | 12 | 12 | 12 |
| AV6403 3.5 mg/ml | Mean | 12475 | 2922 | 935 | 393 | 437 | 66 |
| | (+/−)SEM | 733 | 218 | 47 | 12 | 18 | 3 |
| | N | 12 | 12 | 12 | 12 | 12 | 12 |

TABLE 2

TABLE 2: Striatum turnover ratios of DA and
5-HT following repeated intranasal administration of AV6403.
AV6403 Combined Left and Right Striatum
Turnover Ratios

| TA Code | | DOPAC/ DA | HVA/ DA | (HVA + DOPAC)/DA | 5-H1AA/ 5-HT |
|---|---|---|---|---|---|
| Saline | Mean | 0.23 | 0.08 | 0.31 | 1.08 |
| | (+/−)SEM | 0.01 | 0.00 | 0.02 | 0.03 |
| | N | 12 | 12 | 12 | 12 |
| AV6403 | Mean | 0.28 | 0.08 | 0.36 | 1.28 |
| 1.1 mg/ml | (+/−)SEM | 0.02 | 0.00 | 0.02 | 0.05 |
| | N | 12 | 12 | 12 | 12 |
| AV6403 | Mean | 0.23 | 0.08 | 0.31 | 1.11 |
| 3.5 mg/ml | (+/−)SEM | 0.01 | 0.00 | 0.01 | 0.03 |
| | N | 12 | 12 | 12 | 12 |

TABLE 3

TABLE 3: Substantia nigra levels (ng/g - wet tissue weight) in normal
Fischer 344 rats of DA, DOPAC, HVA, 5-HT, 5-HIAA, and NE
following repeated intranasal administration of AV6403.
AV6403 Combined Left and Right Substantia Nigra
ng/g

| TA Code | | DA | DOPAC | HVA | 5-HT | 5-HIAA | NE |
|---|---|---|---|---|---|---|---|
| Saline | Mean | 1115 | 224 | 115 | 1122 | 565 | 525 |
| | (+/−)SEM | 58 | 19 | 9 | 47 | 34 | 32 |
| | N | 12 | 12 | 12 | 12 | 12 | 12 |
| AV6403 | Mean | 1122 | 232 | 102 | 1014 | 552 | 554 |
| 1.1 mg/ml | (+/−)SEM | 119 | 25 | 10 | 87 | 37 | 56 |
| | N | 12 | 12 | 12 | 12 | 12 | 12 |
| AV6403 | Mean | 1096 | 253 | 113 | 1050 | 546 | 644 |
| 3.5 mg/ml | (+/−)SEM | 70 | 19 | 6 | 84 | 46 | 52 |
| | N | 12 | 12 | 12 | 12 | 12 | 12 |

TABLE 4

TABLE 4: Substantia nigra turnover ratios of DA and
5-HT following repeated intranasal administration of AV6403.
AV6403 Combined Left and Right Substantia Nigra
Turnover Ratios

| TA Code | | DOPAC/ DA | HVA/ DA | (HVA + DOPAC)/DA | 5-HIAA/ 5-HT |
|---|---|---|---|---|---|
| Saline | Mean | 0.20 | 0.10 | 0.30 | 0.50 |
| | (+/−)SEM | 0.01 | 0.01 | 0.01 | 0.02 |
| | N | 12 | 12 | 12 | 12 |
| AV6403 | Mean | 0.22 | 0.15 | 0.37 | 0.58 |
| 1.1 mg/ml | (+/−)SEM | 0.02 | 0.06 | 0.08 | 0.04 |
| | N | 12 | 12 | 12 | 12 |
| AY8403 | Mean | 0.24 | 0.11 | 0.34 | 0.54 |
| 3.5 mg/ml | (+/−)SEM | 0.02 | 0.00 | 0.02 | 0.03 |
| | N | 12 | 12 | 12 | 12 |

Example 9

Glutamate-Alanine-Proline-Phenylalanine-Glutamate-Aspartate-$NH_2$ (SEQ ID NO: 2) Effects on Neurochemistry of the Striatum and Substantia Nigra All animal procedures were conducted in the Laboratory Animal Facilities of the University of Kentucky and approved by the University of Kentucky Institutional Animal Care and Use Committee in agreement with AAALAC guidelines.

Groups of 12, 3 month old Fischer 344 rats were intranasally dosed 50 microliters (4 single 12.5 microliter administrations, 2 per nare, 5 minutes between each nare administration) of either vehicle, 1.2 mg/mL, or 3.6 mg/mL of AV7624 [Glu-Ala-Pro-Phe-Glu-Asp-$NH_2$] once a day for 5 days a week, for 3 weeks (5 consecutive days of dosing, 2 off days, repeated total of 3 times). Following day 21, rats were euthanized and brain tissue was recovered and sections removed and weighed for neurochemical analysis by RP-HPLC EC.

DA, DOPAC, HVA, 5-HT, 5-HIAA, and NE were measured in the striatum and SN for each group. In the striatum [TABLE 5], 3.6 mg/mL dosing of AV7624 led to an approximate 18%, 39%, and 30% reduction of DA, DOPAC, and HVA levels [FIG. 6A-FIG. 6C], respectively, resulting in an about 18% decrease in dopamine turnover ([DOPAC/DA] and [(HVA+DOPAC)/DA]), relative to saline vehicle treated rats [FIG. 7A-FIG. 7B]. Repeated intranasal treatment with 3.6 mg/mL AV7624 resulted in about a 28% and 30% reduction of 5-HT and 5-HIAA levels, with a small effect on turnover [5-HIAA/5-HT, FIG. 8A-FIG. 8B, TABLE 6]. The lower AV7624 dosage had less robust effects on DA, 5-HT and their metabolites [TABLE 5]. NE levels were reduced in the striatum in a dose dependent manner, with about a 32% reduction for the AV7624 3.6 mg/mL dosage versus vehicle [TABLE 5]

Figure 9A:
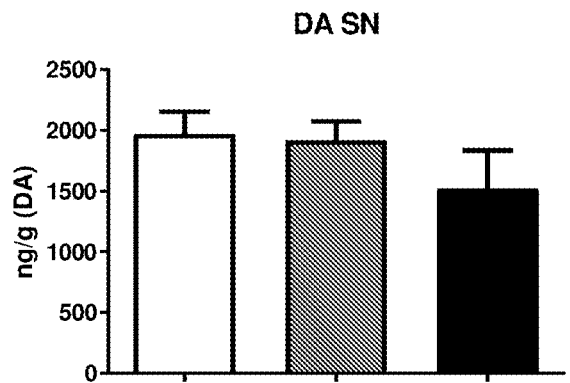
FIG. 9A: Tissue DA levels (ng/g—wet tissue weight) from the entire substantia nigra (both hemispheres) of normal Fischer 344 rats intranasally administered with 50 microliters total of vehicle or AV7624 (1.2 mg/mL or 3.6 mg/mL), 5 days a week for 3 weeks. All data were analyzed by one-way ANOVA and are presented as a mean±SEM, N=12 for vehicle and each AV7624 treatment group.
Figure 9B:
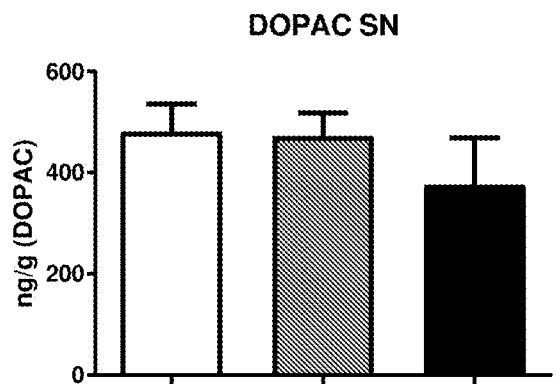
FIG. 9B: Tissue DOPAC levels (ng/g—wet tissue weight) from the entire substantia nigra (both hemispheres) of normal Fischer 344 rats intranasally administered with 50 microliters total of vehicle or AV7624 (1.2 mg/mL or 3.6 mg/mL), 5 days a week for 3 weeks. All data were analyzed by one-way ANOVA and are presented as a mean±SEM, N=12 for vehicle and each AV7624 treatment group.
Figure 9C:
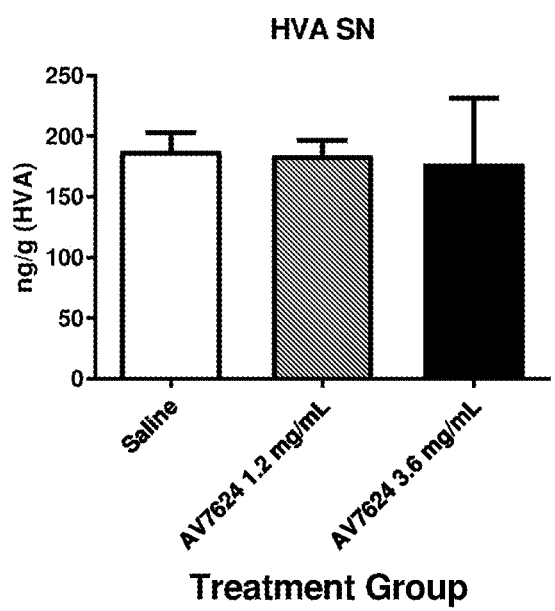
FIG. 9C: Tissue HVA levels (ng/g—wet tissue weight) from the entire substantia nigra (both hemispheres) of normal Fischer 344 rats intranasally administered with 50 microliters total of vehicle or AV7624 (1.2 mg/mL or 3.6 mg/mL), 5 days a week for 3 weeks. All data were analyzed by one-way ANOVA and are presented as a mean±SEM, N=12 for vehicle and each AV7624 treatment group.
Figures 10A, 10B:
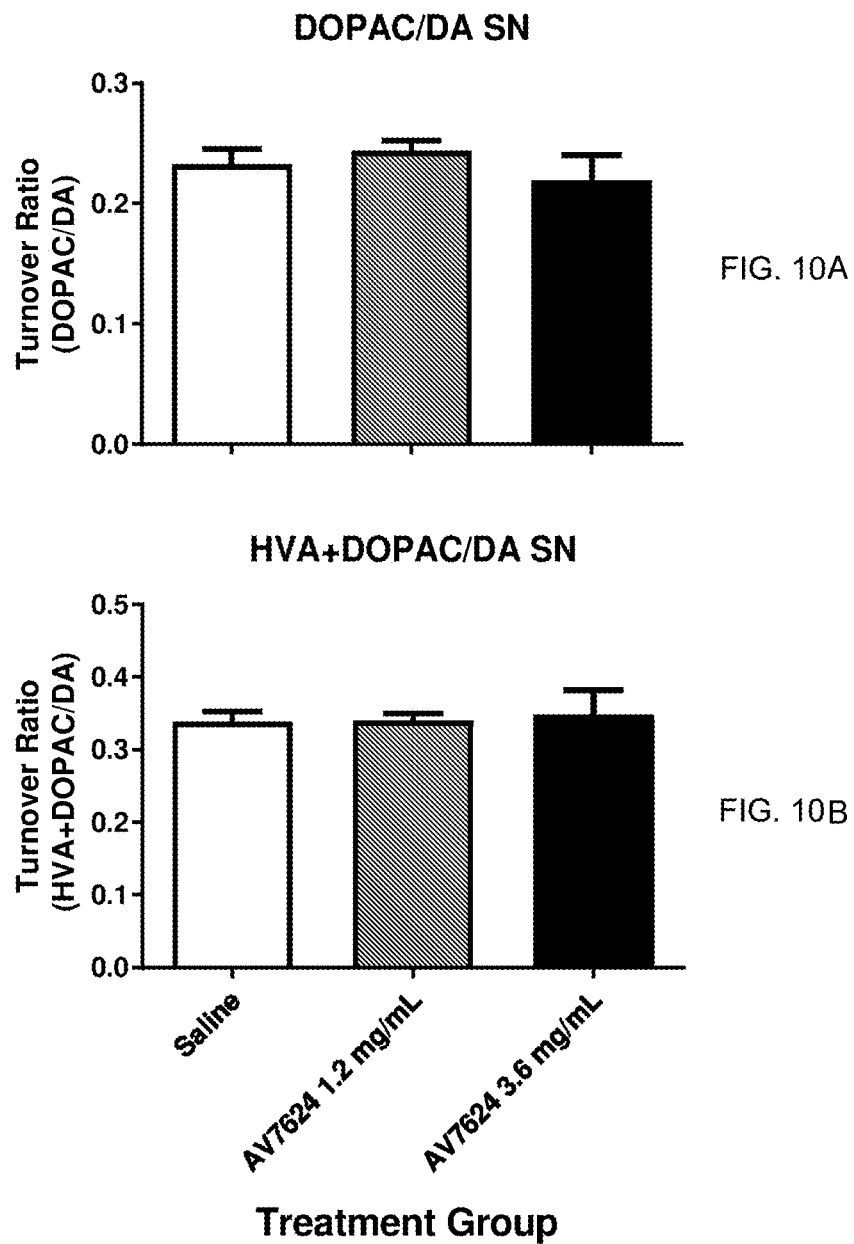
FIG. 10A: DA turnover ratios (DOPAC/DA) of the whole substantia nigra (both hemispheres) of normal Fischer 344 intranasally administered with 50 microliters total of vehicle or AV7624 (1.2 mg/mL or 3.6 mg/mL), 5 days a week for 3 weeks. All data were analyzed by one-way ANOVA and are presented as a mean±SEM, N=12 for vehicle and each AV7624 treatment group.
FIG. 10B: DA turnover ratios ([HVA+DOPAC]/DA) of the whole substantia nigra (both hemispheres) of normal Fischer 344 intranasally administered with 50 microliters total of vehicle or AV7624 (1.2 mg/mL or 3.6 mg/mL), 5 days a week for 3 weeks. All data were analyzed by one-way ANOVA and are presented as a mean±SEM, N=12 for vehicle and each AV7624 treatment group.

In the SN [TABLE 7], treatment with 3.6 mg/mL AV7624 led to about a 23%, 22%, and a 6% decrease in DA, DOPAC, and HVA [FIG. 9A-FIG. 9C], relative to saline vehicle treated rats, with minor effects on dopamine turnover [FIG. 10A-FIG. 10B]. Treatment with 3.6 mg/mL AV7624 decreased 5-HT by 20% and 5-HIAA by about 18% in the SN [TABLE 7], resulting in a minor effect on serotonin turnover [TABLE 8]. NE levels in the SN were decreased (17% and 13%) by both dosages (1.2 mg/mL and 3.6 mg/mL) versus vehicle treated rats, respectively [TABLE 7].

TABLE 5

TABLE 5: Striatum levels (ng/g - wet tissue weight) in normal
Fischer 344 rats of DA, DOPAC, HVA, 5-HT, 5-HIAA, and
NE following repeated intranasal administration of AV7624.
AV7624 Combined Left and Right Striatum
ng/g

| TA Code | | DA | DOPAC | HVA | 5-HT | 5 HIAA | NE |
|---|---|---|---|---|---|---|---|
| AV7624 | Mean | 10762 | 2478 | 915 | 487 | 499 | 67 |
| 3.6 mg/mL | (+/−)SEM | 1405 | 369 | 110 | 51 | 59 | 9 |
| | N | 12 | 12 | 12 | 12 | 12 | 12 |
| Saline | Mean | 13096 | 4077 | 1302 | 679 | 715 | 99 |
| | (+/−)SEM | 569 | 282 | 56 | 46 | 23 | 6 |
| | N | 12 | 12 | 12 | 12 | 12 | 12 |
| AV7624 | Mean | 13521 | 3906 | 1253 | 610 | 674 | 83 |
| 1.2 mg/mL | (+/−)SEM | 689 | 355 | 62 | 48 | 29 | 5 |
| | N | 12 | 12 | 12 | 12 | 12 | 12 |

TABLE 6

TABLE 6: Striatum turnover ratios of DA and 5-HT following repeated intranasal administration of AV7624. AV7624 Combined Left and Right Striatum Turnover Ratios

| TA Code | | DOPAC/ DA | HVA/ DA | (HVA + DOPAC)/DA | 5-HIAA/ 5-HT |
|---|---|---|---|---|---|
| AV7624 | Mean | 0.24 | 0.09 | 0.33 | 1.05 |
| 3.6 mg/mL | (+/−)SEM | 0.02 | 0.00 | 0.02 | 0.05 |
| | N | 12 | 12 | 12 | 12 |
| Saline | Mean | 0.29 | 0.10 | 0.40 | 1.09 |
| | (+/−)SEM | 0.01 | 0.00 | 0.02 | 0.05 |
| | N | 12 | 12 | 12 | 12 |
| AV7624 | Mean | 0.28 | 0.09 | 0.38 | 1.15 |
| 1.2 mg/mL | (+/−)SEM | 0.02 | 0.00 | 0.02 | 0.05 |
| | N | 12 | 12 | 12 | 12 |

TABLE 7

TABLE 7: Substantia nigra levels (ng/g - wet tissue weight) in normal Fischer 344 rats of DA, DOPAC, HVA, 5-HT, 5-HIAA, and NE following repeated intranasal administration of AV7624. AV7624 Combined Left and Right Substantia Nigra ng/g

| TA Code | | DA | DOPAC | HVA | 5-HT | 5-HIAA | NE |
|---|---|---|---|---|---|---|---|
| AV7624 | Mean | 1523 | 376 | 177 | 1251 | 737 | 767 |
| 3.6 mg/mL | (+/−)SEM | 297 | 89 | 52 | 166 | 123 | 187 |
| | N | 12 | 12 | 12 | 12 | 12 | 12 |
| Saline | Mean | 1970 | 480 | 188 | 1566 | 897 | 878 |
| | (+/−)SEM | 178 | 53 | 15 | 86 | 50 | 158 |
| | N | 12 | 12 | 12 | 12 | 12 | 12 |
| AV7624 | Mean | 1918 | 472 | 184 | 1546 | 886 | 727 |
| 1.2 mg/mL | (+/−)SEM | 147 | 44 | 12 | 58 | 26 | 62 |
| | N | 12 | 12 | 12 | 12 | 12 | 12 |

TABLE 8

TABLE 8: Substantia nigra turnover ratios of DA and 5-HT following repeated intranasal administration of AV7624. AV7624 Combined Left and Right Substantia Nigra Turnover Ratios

| TA Code | | DOPAC/ DA | HVA/ DA | (HVA + DOPAC)/DA | 5-HIAA/ 5-HT |
|---|---|---|---|---|---|
| AV7624 | Mean | 0.22 | 0.13 | 0.35 | 0.57 |
| 3.6 mg/mL | (+/−)SEM | 0.02 | 0.02 | 0.03 | 0.03 |
| | N | 12 | 12 | 12 | 12 |
| Saline | Mean | 0.23 | 0.10 | 0.34 | 0.58 |
| | (+/−)SEM | 0.01 | 0.00 | 0.01 | 0.02 |
| | N | 12 | 12 | 12 | 12 |
| AV7624 | Mean | 0.24 | 0.10 | 0.34 | 0.58 |
| 1.2 mg/mL | (+/−)SEM | 0.01 | 0.00 | 0.01 | 0.02 |
| | N | 12 | 12 | 12 | 12 |

Example 10

Distribution of $I^{125}$-radiolabeled Leucine-Alanine-Proline-Tyrosine-Glutamate-Aspartate-NH$_2$ (SEQ ID NO: 3) in the Central Nervous System Following Intranasal Administration.

All animal procedures were conducted in the Laboratory Animal Facilities of the University of Kentucky and approved by the University of Kentucky Institutional Animal Care and Use Committee in agreement with AAALAC guidelines.

Figure 11:
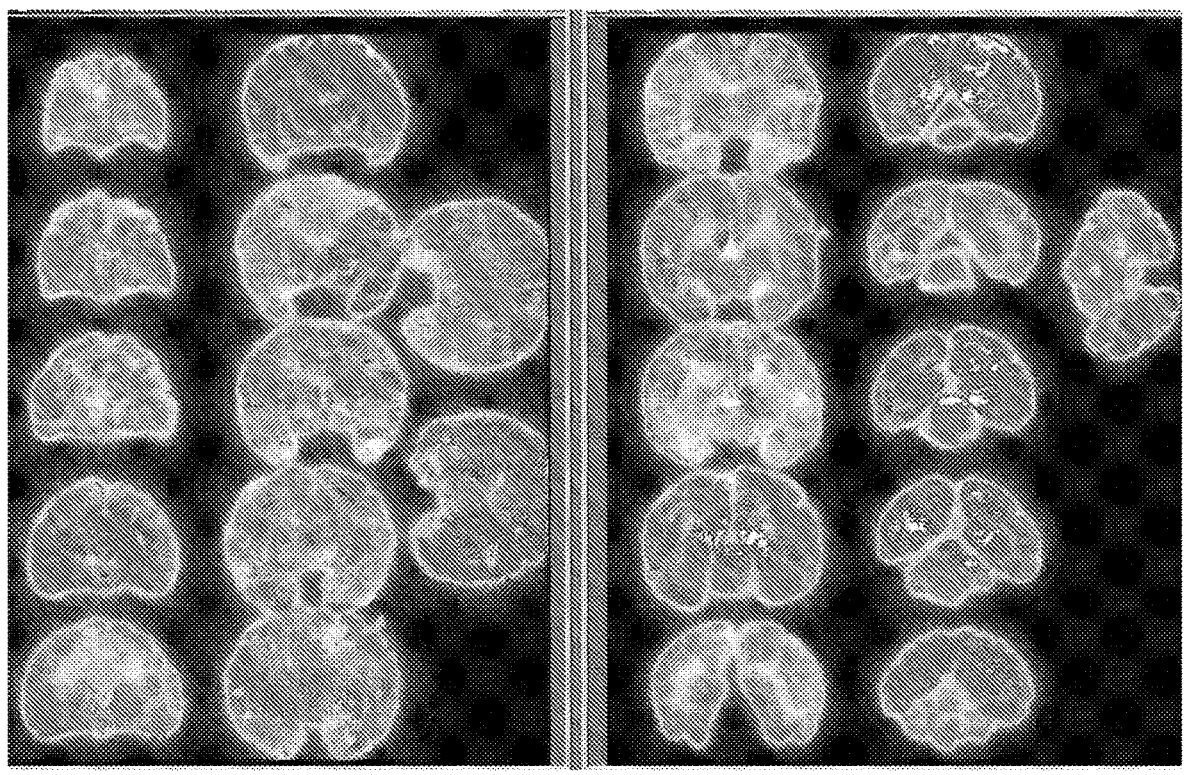
FIG. 11: Autoradiography of $I^{125}$-labeled peptide AV2387 of 2 mm-thick serial coronal slices. The radioactivity signal intensity is color coded from blue (weakest) to red (greatest).
Figure 12:
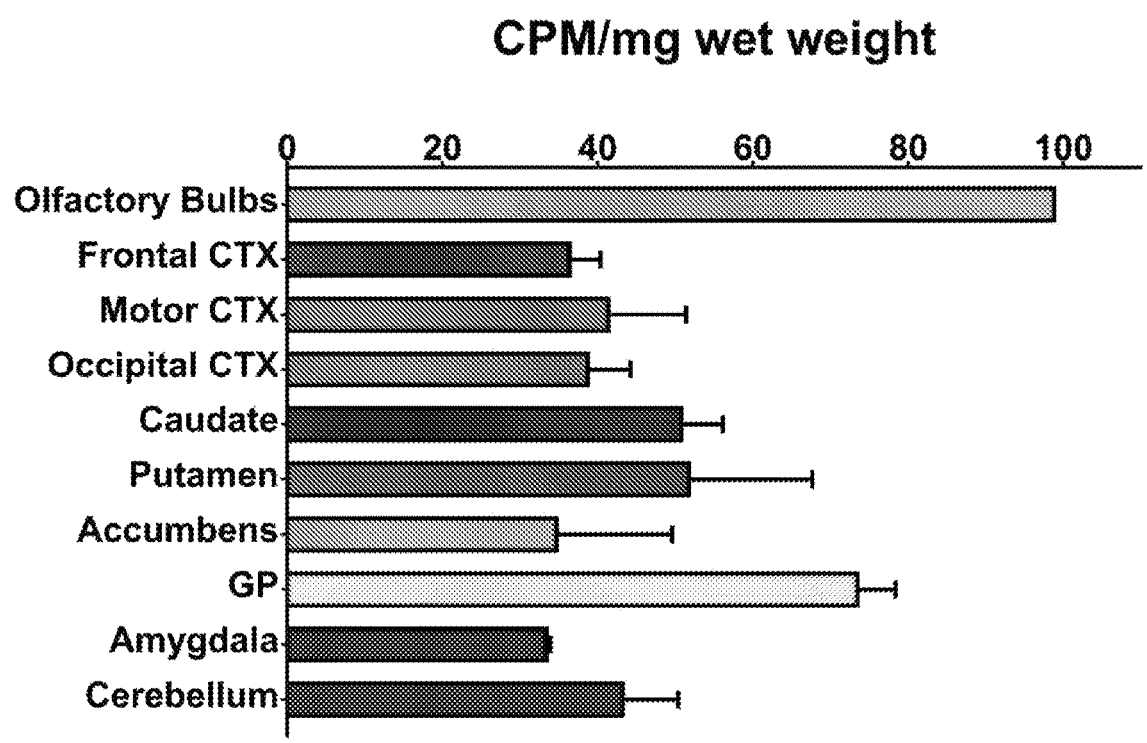
FIG. 12: Tracking of $I^{125}$-labeled peptide AV2387. Gamma counting (CPMs) data are normalized (ng of wet sample tissue weight) 1 hr after a single intranasal administration.

A 10 year old male Rhesus macaque (Non-human primate, NHP) was intranasally administered 10 mgs (5 mgs each nare) of peptide AV2387 [Leu-Ala-Pro-Tyr-Glu-Asp-NH$_2$ (SEQ ID NO: 3)] that was radiolabeled with 5 mCi of $I^{125}$ at the tyrosine residue by the Chloroamine T reaction. At 1 hr following dosing, the NHP was euthanized and transcardially perfused with ice-cold heparinized saline. The whole brain was then harvested and sectioned into 2 mm-thick coronal sections. The olfactory bulb as well as tissue punches from the following brain structures were harvested, weighed and analyzed for distribution by gamma counting: frontal cortex (Frontal CTX), motor cortex (Motor CTX), occipital cortex (Occipital CTX), caudate nucleus (Caudate), putamen, nucleus accumbens (Accumbens), globus pallidus (GP), amygdala, and cerebellum. Radiolabel signal was present throughout the brain [FIG. 11], with the most signal present in the olfactory bulb, globus pallidus, putamen, and caudate nucleus [FIG. 12]. All procedures were conducted in the Laboratory Animal Facilities of the University of Kentucky, which are fully accredited by the Association for Assessment and Accreditation of Laboratory Animal Care.

The pharmacologically active compositions of this invention can be processed in accordance with conventional methods of Galenic pharmacy to produce medicinal agents for administration to subjects, e.g., mammals including humans.

The compositions of this invention individually or in combination are employed in admixture with conventional excipients, i.e., pharmaceutically acceptable organic or inorganic carrier substances suitable for systemic administration. Non-limiting examples of systemic routes of administration include parenteral, enteral (e.g., oral or inhalation) or topical application which do not deleteriously react with the active compositions. Suitable pharmaceutically acceptable carriers include but are not limited to water, salt solutions, alcohols, gum Arabic, vegetable oils, benzyl alcohols, polyethylene glycols, gelatin, carbohydrates such as lactose, amylose or starch, magnesium stearate, talc, titanium dioxide, silicic acid, viscous paraffin, perfume oil, fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compositions. They can also be combined where desired with other active agents, e.g., vitamins.

In some embodiments of the present invention, dosage forms include instructions for the use of such compositions.

For parenteral application, particularly suitable are injectable, sterile solutions, preferably oily or aqueous solutions, as well as suspensions, emulsions, or implants, including suppositories. Ampules, vials, and injector cartridges are convenient unit dosages. For enteral application, particularly suitable are tablets, dragees, liquids, drops, suppositories, or capsules. A syrup, elixir, or the like can be used wherein a sweetened vehicle is employed. Additional systemic administration routes, including intranasal, sublingual, intraocular, and subcutaneous, administration forms are noted.

Sustained or directed release compositions can be formulated, e.g., liposomes or those wherein the active component is protected with differentially degradable coatings, e.g., by microencapsulation, multiple coatings, etc. It is also possible to freeze-dry the new compositions and use the lyophilizates obtained, for example, for the preparation of products for injection.

Generally, the compositions of this invention are dispensed in unit dosage form comprising about 1 to about 100 mg, 200 mg, or 500 mg in a pharmaceutically acceptable carrier per unit dosage.

Example 11

Leucine-Alanine-Proline-Alanine-Glutamate-Aspartate-$NH_2$ (SEQ ID NO: 1) Crossing the Blood Brain Barrier Following Systemic Delivery.

Figure 13A:
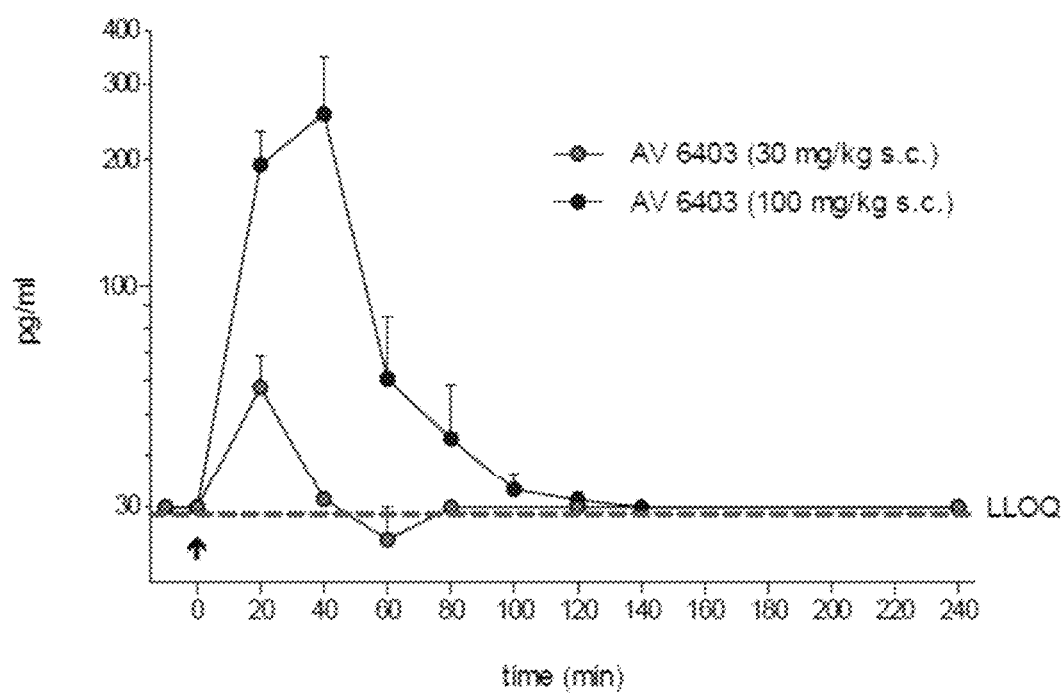
FIG. 13A is a graph showing the extracellular brain levels of AV6403 over time following its subcutaneous (s.c.) administration at 30 mg/kg (n=2) and 100 mg/kg (n=2). Y-axis units in log ng/ml.
Figure 13B:
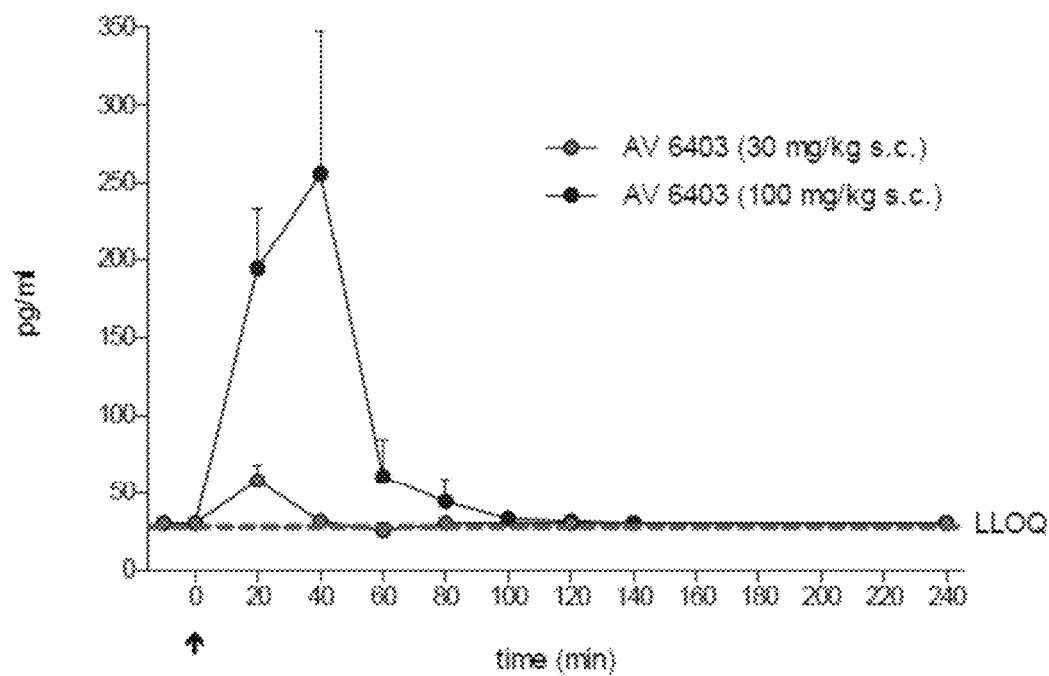
FIG. 13B shows the extracellular brain levels of AV6403 over time following its subcutaneous (s.c.) administration at 30 mg/kg (n=2) and 100 mg/kg (n=2). Y-axis units in linear ng/ml.
Figure 14:
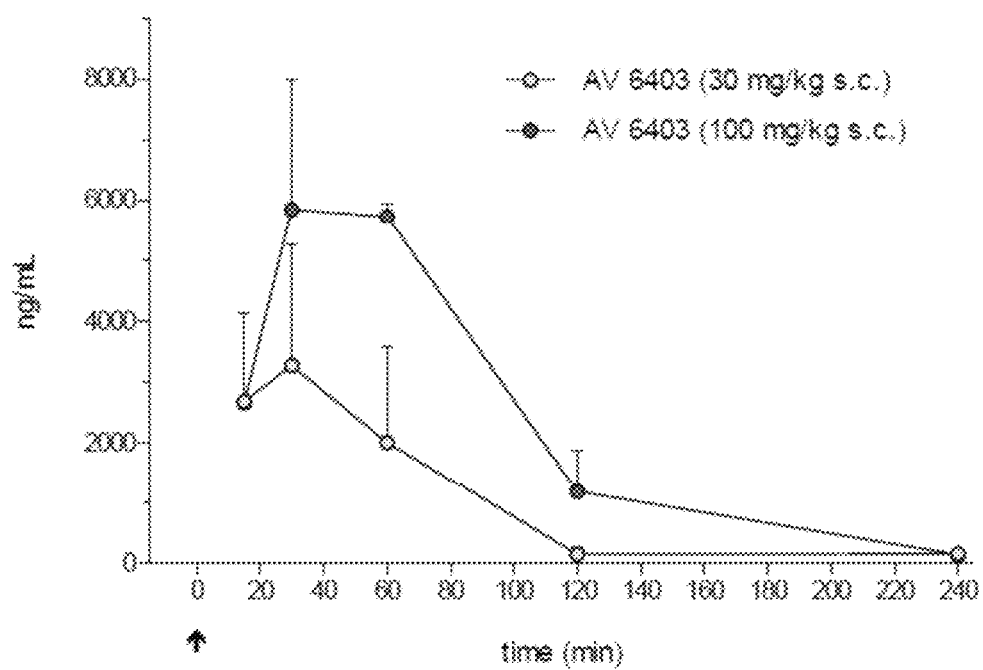
FIG. 14 shows plasma levels of AV6403 over time following its subcutaneous administration at time 0 for 30 and 100 mg/kg AV6403 as measured using LC-MS/MS. Y-axis units in linear ng/ml.

Extracellular brain levels were seen to rise and fall to baseline by 140 minutes post injection following subcutaneous administration of AV6403 [LAPAED-NH2 (SEQ ID NO: 1)] as measured using liquid chromatography mass spectrometry/mass spectrometry (LC-MS/MS) seen in FIG. 13A and FIG. 13B. The AV6403 was identified by mass ion and use of deuterated internal standard. AV6403 was present across the blood brain barrier in the extracellular space of the rat brain following systemic delivery in a dose-dependent manner, with maximum levels observed (250 pg/mL and 50 pg/mL for 100 mg/kg and 30 mg/kg dosages in saline buffer, respectively) between 20-40 minutes post administration as measured by in vivo striatal microdialysis in awake animals (FIG. 13A and FIG. 13B). The $T_{1/2}$ was between 50-60 minutes with a total lifetime in the extracellular space of the brain ~120 minutes. Plasma blood levels (FIG. 14) were consistent with higher levels with maximum levels (6000 ng/ML and 3500 ng/mL for 100 mg/kg and 30 mg/kg, respectively) reached between 20-40 minutes post administration, and a longer lifetime as compared to the extracellular brain levels.

Example 12

Glutamate-Alanine-Proline-Alanine-Glutamate-NH2 (SEQ ID NO: 10) Entering the Brain Following Systemic Delivery.

Figure 15:
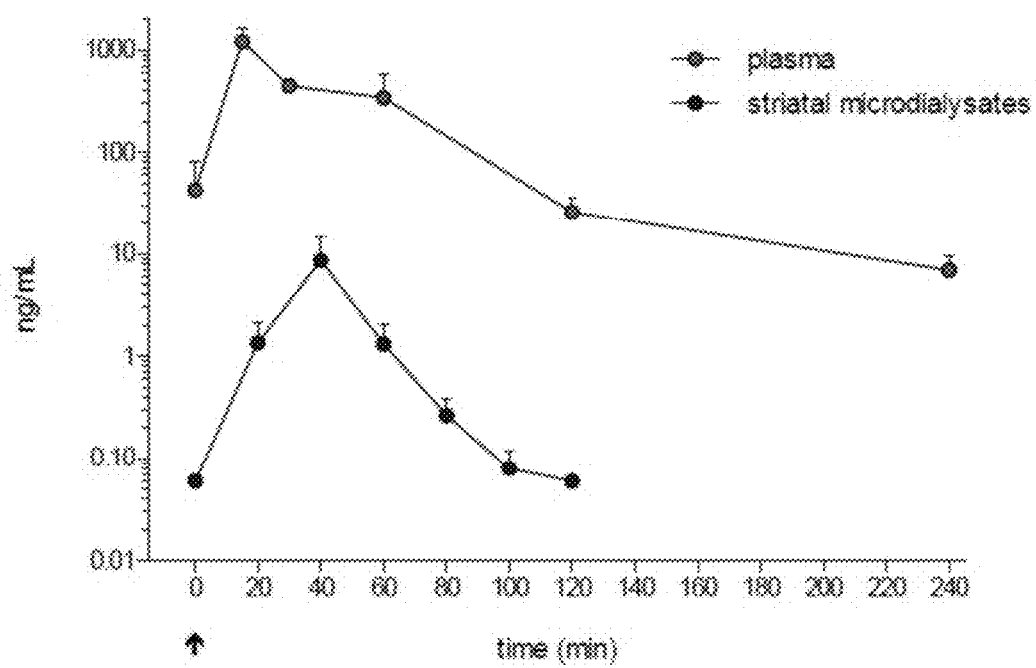
FIG. 15 shows plasma and extracellular brain levels of AV2157 over time in awake rats measured using (LC-MS/MS) following s.c. administration. Y-axis units in log ng/ml.
Figure 16:
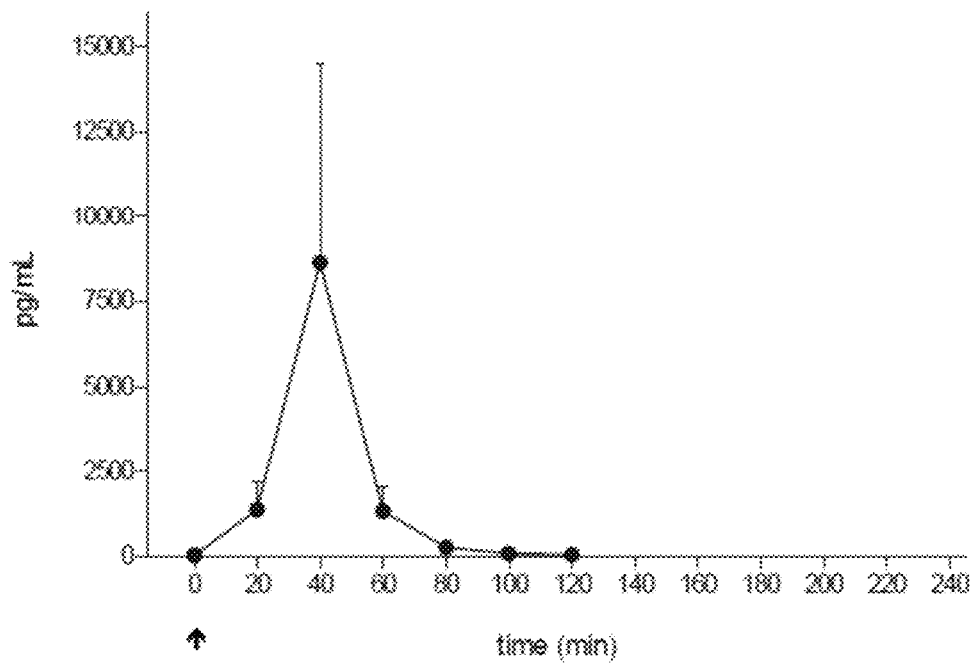
FIG. 16 is a graph showing the extracellular brain levels of AV2157 over time in awake rats measured using LC-MS/MS following subcutaneous administration at 100 mg/kg. Y-axis units in linear ng/ml.
Figure 17:
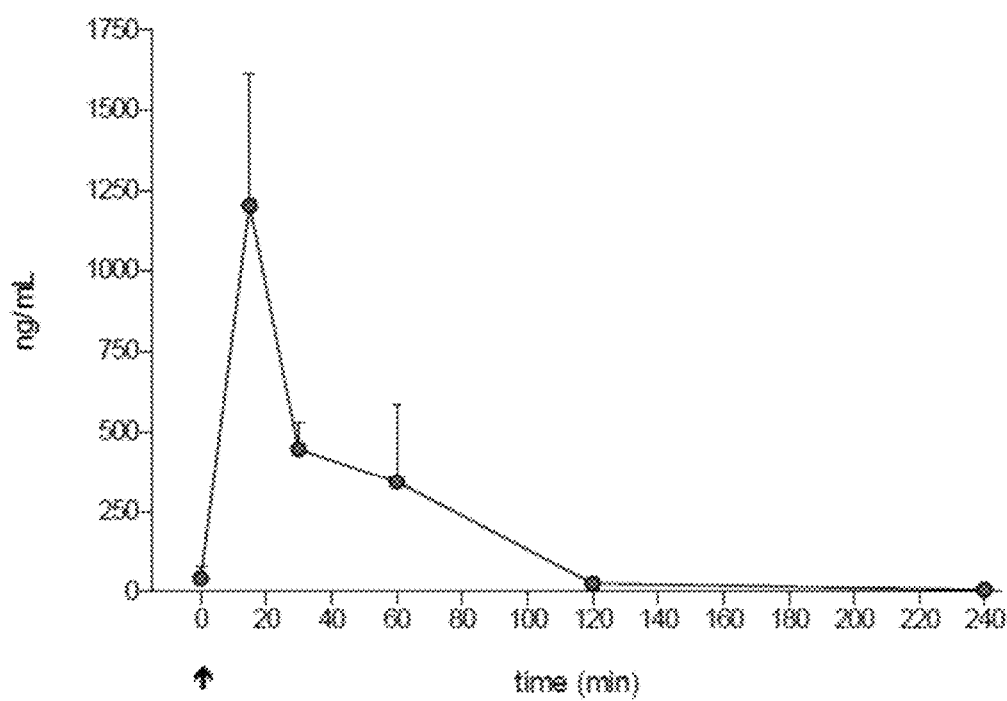
FIG. 17 shows plasma levels of AV2157 over time in awake rats (n=2) measured using LC-MS/MS following s.c. administration at 100 mg/kg. Y-axis units in linear ng/ml.
Figure 18A:
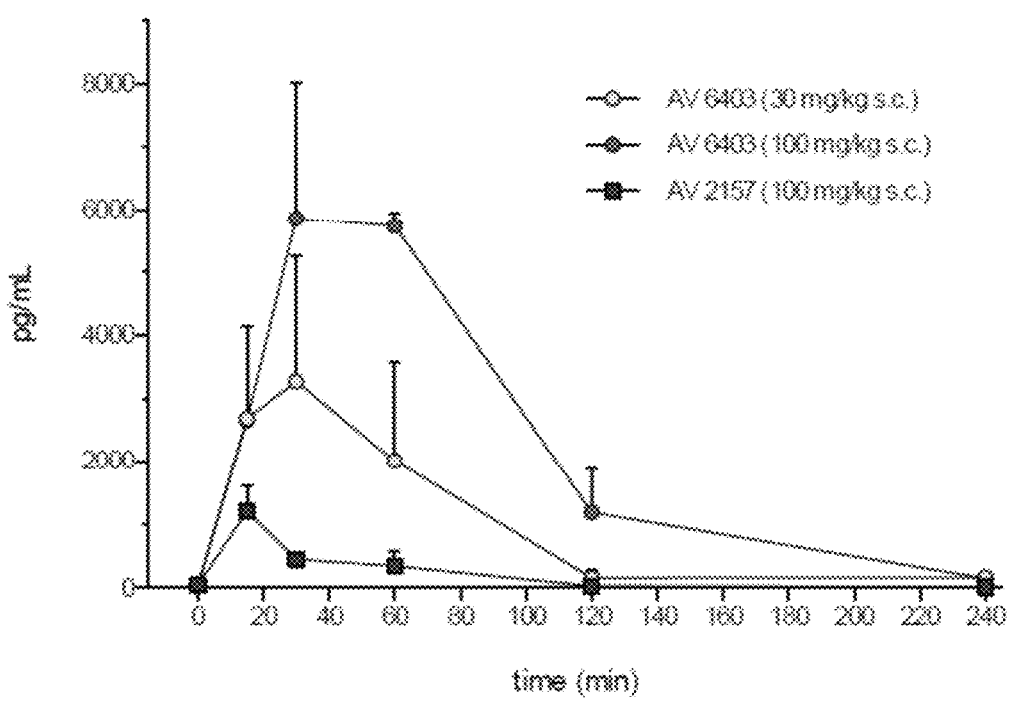
FIG. 18A depicts a plot showing the plasma levels of AV6403 administered at 30 and 100 mg/kg and AV2157 administered at 100 mg/kg over time following s.c. administration. Y-axis units in log ng/ml.
Figure 18B:
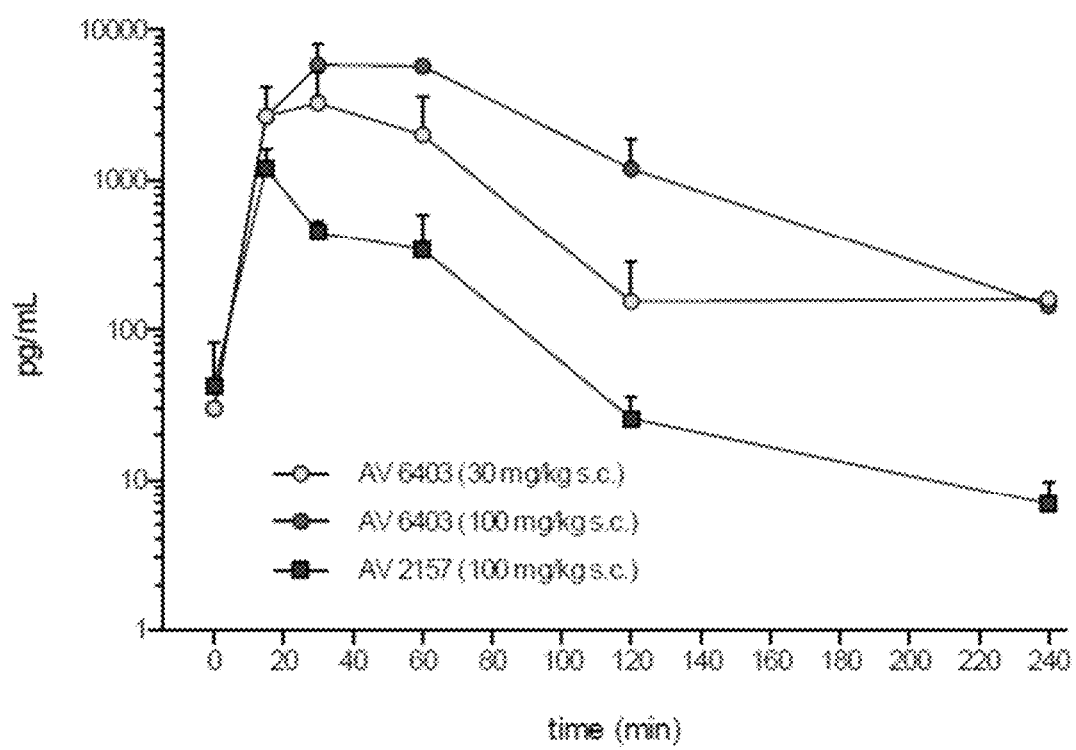
FIG. 18B depicts a plot showing the plasma levels of AV6403 administered at 30 and 100 mg/kg and AV2157 administered at 100 mg/kg over time following s.c. administration. Y-axis units in linear ng/ml.
Figure 19A:
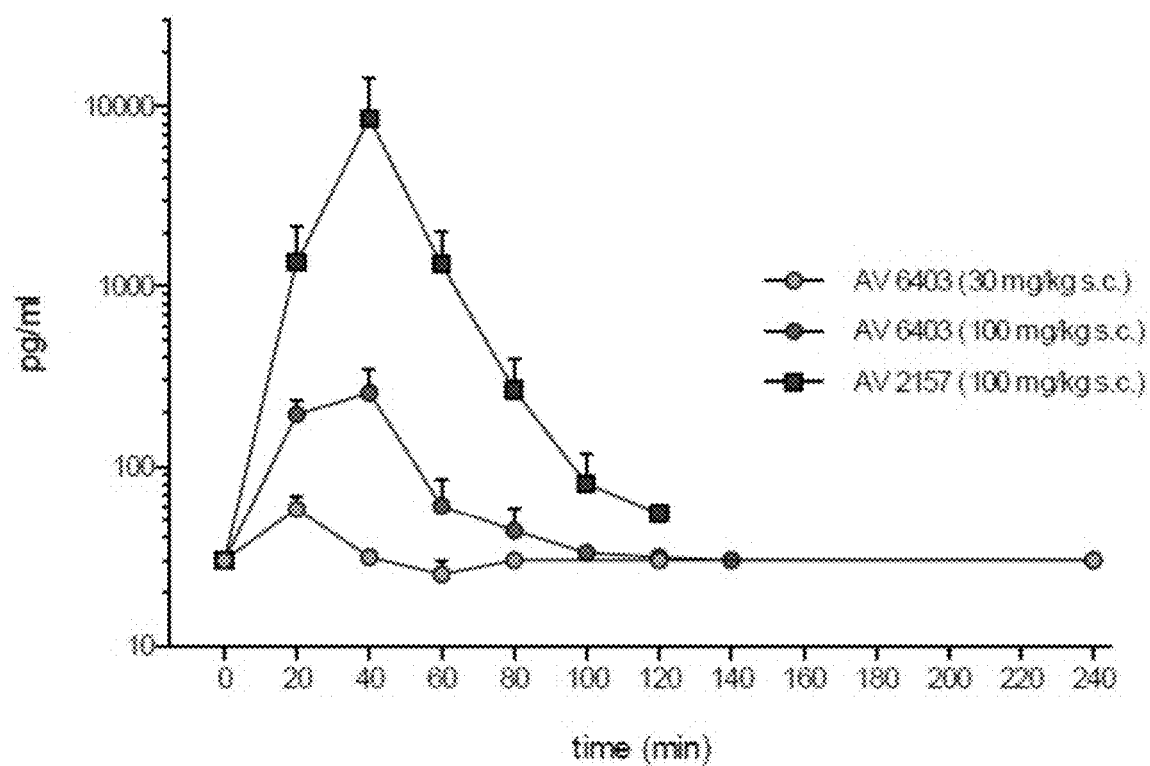
FIG. 19A shows the extracellular brain levels of AV6403 administered at 30 and 100 mg/kg and AV2157 administered at 100 mg/kg over time following s.c. administration. Y-axis units in log ng/ml.
Figure 19B:
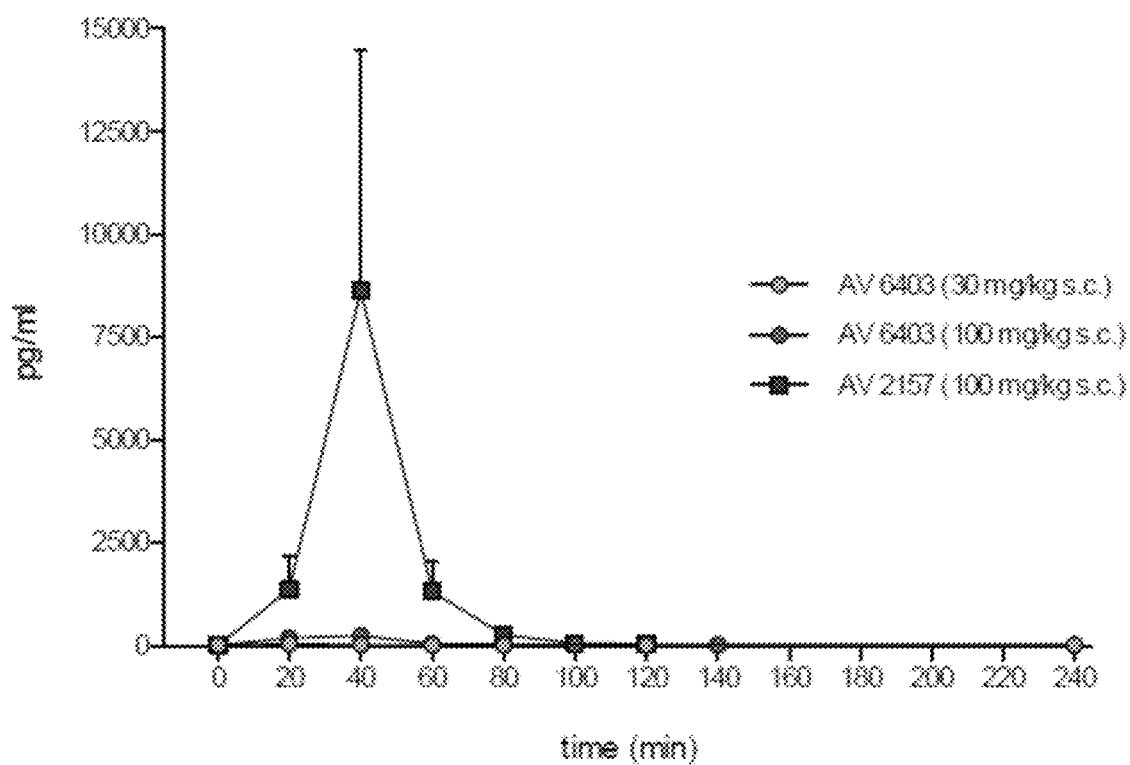
FIG. 19B shows the levels of extracellular brain levels of AV6403 administered at 30 and 100 mg/kg and AV2157 administered at 100 mg/kg over time following s.c. administration. Y-axis units in linear ng/ml.

AV2157 [EAPAE-NH2 (SEQ ID NO: 10)] was observed to cross the blood brain barrier at 100 mg/kg dosage in saline, with maximum levels in the extracellular space observed at 40 minutes (9 ng/mL) post subcutaneous administration, with a T1/2 between 50-60 minutes and a total lifetime of ~120 minutes, as measured by in vivo striatal microdialysis in awake rats (FIG. 15, FIG. 16). AV2157 plasma levels (FIG. 3, FIG. 5) reached maximum level at 20 minutes (1250 ng/mL) post administration of 100 mg/kg dosage in saline, with a total lifetime of ~120 minutes. This plasma profile is similar compared to AV6403 (FIG. 15, FIG. 18A and FIG. 18B), but with improved (over 10 times) CNS bioavailability (FIG. 16, FIG. 19A and FIG. 19B).

SEQUENCE TABLE:

| SEQ ID NO | Sequence | Description. |
|---|---|---|
| 1 | Leu-Ala-Pro-Ala-Glu-Asp | AMIDATION at position 6. |
| 2 | Glu-Ala-Pro-Phe-Glu-Asp | AMIDATION at position 6. |
| 3 | Leu-Ala-Pro-Tyr-Glu-Asp | AMIDATION at position 6. |
| 4 | Leu-Gly-Pro-Phe-Ser-Glu | AMIDATION can be either present or absent at position 6. |
| 5 | Cys-Leu-Gly-Pro-Phe-Ser-Glu-Cys | Cyclic peptide |
| 6 | Trp-Xaa$_2$-Pro-Xaa$_4$-Asp | AMIDATION at position 5. Xaa$_2$ is D-Ala. Xaa$_4$ is D-Lys. |
| 7 | Xaa$_1$-Ala-Pro-Phe-Xaa$_5$-Gly | AMIDATION at position 6. Xaa$_1$ is D-Glu. Xaa$_5$ is D-Ala. |

SEQUENCE TABLE:

| SEQ ID NO | Sequence | Description. |
|---|---|---|
| 8 | Glu-Xaa$_2$-Pro-Xaa$_4$-Xaa$_5$ | AMIDATION at position 5.<br>Xaa$_2$ is deuterated Lys.<br>Xaa$_4$ is D-Phe.<br>Xaa$_5$ is deuterated leu |
| 9 | Xaa$_1$-Xaa$_2$-Pro-Ala-Xaa$_5$-Phe | Xaa$_1$ is acylated-Leu<br>Xaa$_2$ is D-Met.<br>Xaa$_5$ is deuterated Ser. |
| 10 | Glu-Ala-Pro-Ala-Glu | AMIDATION at position 5. |
| 11 | Glu-Ala-Pro-Ala-Glu-Asp | AMIDATION at position 6. |
| 12 | Xaa$_1$-Xaa$_2$-Xaa$_3$-Xaa$_4$-Xaa$_5$ | Xaa$_1$ is leucine, tryptophan or glutamate.<br>Xaa$_2$ is glycine, lysine, leucine, methionine, tryptophan or alanine.<br>Xaa$_3$ is Proline<br>Xaa$_4$ is phenylalanine, lysine, leucine, tryptophan, tyrosine or alanine.<br>Xaa$_5$ is alanine, cysteine, aspartate, leucine, methionine, asparagine, serine or glutamate. |
| 13 | Xaa$_1$-Xaa$_2$-Xaa$_3$-Xaa$_4$-Xaa$_5$-Xaa$_6$ | Xaa$_1$ is leucine, tryptophan or glutamate.<br>Xaa$_2$ is glycine, lysine, leucine, methionine, tryptophan or alanine.<br>Xaa$_3$ is Proline.<br>Xaa$_4$ is phenylalanine, lysine, leucine, tryptophan, tyrosine or alanine.<br>Xaa$_5$ is alanine, cysteine, aspartate, leucine, methionine, asparagine, serine or glutamate.<br>Xaa$_6$ is alanine, cysteine, glutamate, phenylalanine, glycine, leucine, proline, serine, or aspartate. |
| 14 | Trp-Ala-Pro-Ala-Glu-Asp | |
| 15 | Glu Gly Pro Ala Glu Asp | |
| 16 | Glu Lys Pro Ala Glu Asp | |
| 17 | Glu Leu Pro Ala Glu Asp | |
| 18 | Glu Met Pro Ala Glu Asp | |
| 19 | Glu Trp Pro Ala Glu Asp | |
| 20 | Glu Ala Pro Lys Glu Asp | |
| 21 | Glu Ala Pro Leu Glu Asp | |
| 22 | Glu Ala Pro Trp Glu Asp | |
| 23 | Glu Ala Pro Ala Ala Asp | |
| 24 | Glu Ala Pro Ala Cys Asp | |
| 25 | Glu Ala Pro Ala Asp Asp | |
| 26 | Glu Ala Pro Ala Leu Asp | |
| 27 | Glu Ala Pro Ala Met Asp | |
| 28 | Glu Ala Pro Ala Asn Asp | |

-continued

SEQUENCE TABLE:

| SEQ ID NO | Sequence | Description |
|---|---|---|
| 29 | Glu Ala Pro Ala Ser Asp | |
| 30 | Glu Ala Pro Ala Glu Ala | |
| 31 | Glu Ala Pro Ala Glu Cys | |
| 32 | Glu Ala Pro Ala Glu Glu | |
| 33 | Glu Ala Pro Ala Glu Phe | |
| 34 | Glu Ala Pro Ala Glu Gly | |
| 35 | Glu Ala Pro Ala Glu Leu | |
| 36 | Glu Ala Pro Ala Glu Pro | |
| 37 | Glu Ala Pro Ala Glu Ser | |
| 38 | Glu Gly Pro Ala Ala | |
| 39 | $Xaa_1$-$Xaa_2$-$Xaa_3$-$Xaa_4$-$Xaa_5$ | $Xaa_1$ is any amino acid. $Xaa_2$ is any amino acid. $Xaa_3$ is proline. $Xaa_4$ is any amino acid. $Xaa_5$ is any amino acid. |
| 40 | $Xaa_1$-$Xaa_2$-$Xaa_3$-$Xaa_4$-$Xaa_5$-$Xaa_6$ | $Xaa_1$ is any amino acid. $Xaa_2$ is any amino acid. $Xaa_3$ is proline. $Xaa_4$ is any amino acid. $Xaa_5$ is any amino acid. $Xaa_6$ is any amino acid. |

REFERENCES

Reference is made to the following publications, the teachings of which are herein incorporated by reference in their entirety as are all publications cited herein:

1. "The cyclization of peptides and depsipeptides," Davies Ed., *J Peptide Science,* 9(8) 471-501 (2003);
2. Baert F, Noman M, Vermeire S, Van Assche G, D'Haens G, Carbonez A, Rutgeerts P. Influence of immunogenicity on the long term efficacy of infliximab in Crohn's Disease. N Engl J Med 348: 601 608 (2003).
3. Baker M, Reynolds H M, Lumicisi B, Bryson C J. Immunogenicity of protein therapeutics: The key causes, consequences and challenges. Self/Nonself 1(4). (2010).
4. Ben M. Dunn (Ed), *Peptide Chemistry and Drug Design* 1st Edition, Wiley; 1 edition (Mar. 9, 2015);
5. Bendtzen K, Geborek P, Svenson M, Larsson L, Kapetanovic M C, Saxne T. Individualized monitoring of drug bioavailability and immunogenicity in rheumatoid arthritis patients treated with the tumor necrosis factor A inhibitor infliximab. Arthritis Rheumatology 54:3782 3789 (2006).
6. Brooks D A, Kakavanos R, Hopwood J J. Significance of immune response to enzyme replacement therapy for patients with a lysosomal storage disorder. Trends in Molecular Medicine 9:450 453 (2003).
7. Büttel IC, Chamberlain P, Chowers Y, Ehmann F, Greinacher A, Jefferis R, Kramer D, Kropshofer H, Lloyd P, Lubiniecki A, Krause R, Mire Sluis A, Platts Mills T, Ragheb J A, Reipert B M, Schellekens H, Seitz R, Stas P, Subramanyam M, Thorpe R, Trouvin J. H., Weise M, Windisch J, Schneider C K. Taking immunogenicity assessment of therapeutic proteins to the next level. Biologicals 39:100 109 (2011).
8. Casadevall N, Nataf J, Viron B, Kolta A, Kiladjian J J., Martin Dupont P, Michaud P, Papo T, Ugo V, Teyssandier I, Varet B, Mayeux P. Pure red cell aplasia and antierythropoietin antibodies in patients treated with recombinant erythropoietin. N Engl J Med 346: 469 475 (2002).
9. Chapman et al., "Intranasal treatment of central nervous system dysfunction in humans," *Pharm Res.* 2013 October; 30(10):2475 84. doi: 10.1007/s11095 012 0915 1.
10. Choi et al., "Specific modulation of dopamine expression in neuronal hybrid cells by primary cells from different brain regions,"*Proc Natl Acad Sci USA;* 89(19): 8943 7. (1992)
11. Durelli L, Ricci A. Anti interferon antibodies in multiple sclerosis. Molecular basis and their impact on clinical efficacy. Front Biosci 9: 2192 2204 (2004).
12. Fineman M S, Mace K F, Diamant M, Darsow T, Cirincione B B, Booker Porter T K, Kinninger L A, Trautmann M E. Clinical relevance of anti exenatide antibodies: safety, efficacy and cross reactivity with long term treatment. Diabetes, Obesity and Metabolism 14: 546 554 (2012).
13. Fortuna et al., "Intranasal delivery of systemic acting drugs: small molecules and biomacromolecules,". Eur J Pharm Biopharm. 2014 September; 88(1):8 27. doi: 10.1016/j.ejpb.2014.03.004. Epub 2014 Mar. 28;
14. Hansel T T, Kropshofer H, Singer T, Mitchell J A, George A J T. The safety and side effects of monoclonal antibodies. Nature Reviews Drug Discovery 9: 325 338 (2010).
15. Hanson "Intranasal administration of CNS therapeutics to awake mice," J Vis Exp 74(e4440):17, 2013);

16. Joo "Cyclic Peptides as Therapeutic Agents and Biochemical Tools," Biomol Therap, 20 (1): 19 26 (2012). doi: 10.4062/biomolther.2012.20.1.019
17. Kim Y, Ponomarenko J, Zhu Z, Tamang D, Wang P, Greenbaum J, Lundegaard C, Sette A, Lund O, Bourne P E, Nielsen M, Peters B. Immune epitope database analysis resource. *Nucleic Acid Res.* 40: W525 530 (2012). doi: 10.1093/nar/gks438
18. Krishna M, Nadler S G. Immunogenicity to biotherapeutics—the role of anti drug immune complexes. Fron. Immunol. 00021 (2016).
19. Leach M W, Rottman J B, Hock M B, Finco D, Rojko J L, Beyer J C. Immunogenicity/hypersensitivity of biologics. Toxicol Pathol 42: 293 300 (2014).
20. Lukhanina et al., "Effect of cerebrolysin on the electroencephalographic indices of brain activity in Parkinson's disease", Zh Nevrol Psikhatr Im S S Korsakova 104: 54 60 (2004)
21. Meredith et al., "Intranasal Delivery of Proteins and Peptides in the Treatment of Neurodegenerative Diseases," *AAPS J.* 2015 July; 17(4):780 7. doi: 10.1208/s12248 015 9719 7. Epub 2015 Mar. 24;
22. Newman et al., "Drug Delivery to the Nasal Cavity: In vitro and In vivo Assessment", DOI: 10.1615/CritRevTherDrugCarrierSyst.v21.i1.20.
23. Ohshima Hosoyama S, Simmons H A, Goecks N, Joers V, Swanson C R, Bondarenko V, Velotta R, Brunner K, Wood L D, Hruban R H, Emborg M E. A monoclonal antibody GDNF fusion protein is not neuroprotective and is associated with proliferative pancreatic lesions in parkinsonian monkeys. PLoS One 2012: 7(6) e39036.
24. PG Djupesland "Nasal drug delivery devices: characteristics and performance in a clinical perspective—a review," Drug Deliv Transl Res 2013 February; 3(1): 42-62. doi: 10.1007/s13346 012 0108 9
25. Prescott R, Nakai H, Saenko E L, Scharrer I, Nilsson I M, Humphries J E, Hurst D, Bray G, Scandella D. The inhibitor antibody response is more complex in hemophilia A patients than in most nonhemophilicas with factor VIII autoantibodies. Recombinate and Kogenate study groups. Blood 89: 3663 3671 (1997).
26. Richards J, Auger J, Peace D, Gale D, Michel J, Koons A, Haverty T, Zivin R, Jolliffe L, Bluestone J A. Phase I evaluation of humanized OKT3: toxicity and immunomodulatory effects of hOKT3gamma4. Cancer Res 59: 2096 2101 (1999).
27. Rojko J L, Evans M G, Price S A, Han B, Waine G, DeWitte M, Haynes J, Freimark B, Martin P, Raymond J T, Evering W, Rebelatto M C, Schenck E, Horvath. Formation, clearance, deposition, pathogenicity, and identification of biopharmaceutical related immune complexes. Toxicologic Pathology 42: 725 764 (2014)
28. Scharrer I. Recombinant Factor VIIA for patients with inhibitors to Factor VIII or IX or Factor VII deficiency. Haemophilia 5: 253 259 (1999).
29. Schellekens H. The immunogenicity of therapeutic proteins. *Discov Med.* 9:560 564 (2010).
30. Schmidt E, Hennig K, Mengede C, Zillikens D, Kromminga A. Immunogenicity of rituximab in patients with severe pemphigus. Clin Immunol. 132: 334 341 (2009).
31. Spetter et al., "Intranasal Neuropeptide Administration to Target the Human Brain in Health and Disease," *Mol Pharm.* 2015 Aug. 3; 12(8):2767 80. doi: 10.1021/acs.molpharmaceut.5b00047. Epub 2015 Apr. 28;
32. Stoever J A, Palmer J P. Inhaled insulin and insulin antibodies: a new twist to an old debate. Diabetes Technol Ther 4: 157 161 (2002).
33. Tatarewicz S M, Wei X, Gupta S, Masterman D, Swanson S J, Moxness M S. Development of a maturing T cell mediated immune response in patients with idiopathic Parkinson's disease receiving r metHuGDNF via continuous intraputaminal infusion. J Clin Immun 27: 620 7.
34. Thorne et al., "Delivery of interferon beta to the monkey nervous system following intranasal administration," *Neuroscience*, March 27; 152(3):785 97, doi: 10.1016/j.neuroscience.2008.01.013. Epub 2008, Jan. 16 2008);
35. Wagner C L, Schantz A, Barnathan E, Olson A, Mascelli M A, Ford J, Damaraju L, Schaible T, Maini R N, Tcheng J E. Consequences of immunogenicity to the therapeutic monoclonal antibodies ReoPro and Rem icade. Dev Biol (Basel) 112: 37 53 (2003).
36. Weber et al., "Antioxidants, supplements and Parkinson's disease", Ann Pharacother 40: 935 938 (2006).
37. Wermeling et al., "Pharmacokinetics, bioequivalence, and spray weight reproducibility of intranasal butorphanol after administration with 2 different nasal spray pumps." *J Clin Pharmacol.* 2005 August; 45(8):969 73.
38. Wriggers et al., "Control of protein functional dynamics by peptide linkers,". *Biopolymers.* 2005; 80(6):736 46;
39. Yu Sung Chen et al., "An intranasally delivered peptide drug ameliorates cognitive decline in Alzheimer transgenic mice," *EMBO Mol Med.* 2017 May; 9(5): 703-715.

The invention claimed is:

1. A 5- or 6-amino acid therapeutic peptide having an amino acid sequence selected from the group consisting of SEQ ID NOs: 1-11.

2. The therapeutic peptide of claim 1, wherein one or more amino acid of the therapeutic peptide is a D-amino acid.

3. The therapeutic peptide of claim 1, wherein the C-terminus of the therapeutic peptide is modified to include substituents selected from the group consisting of amidation, dansyl, lipoic acids, succinylation.

4. The therapeutic peptide of claim 1, wherein the N-terminus of the therapeutic peptide is modified to include substituents selected from the group consisting of acetyl, dansyl, lipoic acids, succinylation.

5. The therapeutic peptide of claim 1, wherein the therapeutic peptide is deuterized.

6. The therapeutic peptide of claim 1, wherein the therapeutic peptide is cyclized by the addition of terminal cysteines.

* * * * *